US010570199B2

(12) United States Patent
Shimizu et al.

(10) Patent No.: US 10,570,199 B2
(45) Date of Patent: Feb. 25, 2020

(54) HUMAN ANTIBODY AGAINST IL-18

(71) Applicant: KM Biologics Co., Ltd., Kumamoto-shi, Kumamoto (JP)

(72) Inventors: Hiroyuki Shimizu, Kikuchi (JP); Miyuki Matsumoto, Kikuchi (JP); Kenji Soejima, Kikuchi (JP); Masaharu Torikai, Kikuchi (JP); Toshihiro Nakashima, Kikuchi (JP)

(73) Assignee: KM Biologics Co., Ltd., Kumamoto (JP)

( * ) Notice: Subject to any disclaimer, the term of this patent is extended or adjusted under 35 U.S.C. 154(b) by 1315 days.

(21) Appl. No.: 14/442,004

(22) PCT Filed: Nov. 18, 2013

(86) PCT No.: PCT/JP2013/081057
§ 371 (c)(1),
(2) Date: May 11, 2015

(87) PCT Pub. No.: WO2014/080866
PCT Pub. Date: May 30, 2014

(65) Prior Publication Data
US 2019/0077858 A1    Mar. 14, 2019

(30) Foreign Application Priority Data
Nov. 21, 2012   (JP) ................. 2012-254893

(51) Int. Cl.
C07K 16/24      (2006.01)
A61P 37/06      (2006.01)
G01N 33/68      (2006.01)
C12N 15/10      (2006.01)
C12N 15/62      (2006.01)
G01N 33/538     (2006.01)
G01N 33/543     (2006.01)

(52) U.S. Cl.
CPC ............ *C07K 16/244* (2013.01); *A61P 37/06* (2018.01); *C12N 15/1037* (2013.01); *C12N 15/62* (2013.01); *G01N 33/538* (2013.01); *G01N 33/54353* (2013.01); *G01N 33/6857* (2013.01); *G01N 33/6869* (2013.01); *C07K 2317/21* (2013.01); *C07K 2317/33* (2013.01); *C07K 2317/622* (2013.01); *C07K 2317/76* (2013.01)

(58) Field of Classification Search
None
See application file for complete search history.

(56) References Cited

U.S. PATENT DOCUMENTS 6,706,487 B1    3/2004   Abdel-Meguid et al.
9,255,144 B2 *  2/2016   Dobson ............... C07K 16/244

2005/0074434 A1    4/2005   Hoshino et al.
2005/0100965 A1    5/2005   Ghayur et al.
2007/0292432 A1   12/2007   Ellis et al.
2014/0004128 A1 *  1/2014   Dobson ............... C07K 16/244
                                                         424/158.1

FOREIGN PATENT DOCUMENTS

EP      1621616          2/2006
EP      2395020         12/2011
JP      2004-500086      1/2004
WO      2004/097019     11/2004
WO      2008/007648      1/2008
WO   WO-2012085015 A9 *  6/2013 ........... C07K 16/244

OTHER PUBLICATIONS

Vajdos et al. (J Mol Biol. Jul. 5, 2002;320(2):415-28 (Year: 2002).*
Brown et al. (J Immunol. May 1996;156(9):3285-91 (Year: 1996).*
Ma (Modern Drug Discovery 2004, 7(6)) (Year: 2004).*
Steinman et al (Nat Med. Jan. 6, 2012;18(1):59-65) (Year: 2012).*
Blumberg et al (Nat Med.; 18(1): 35-41) (Year: 2015).*
Gao et al, "Construction of murine phage antibody library and selection of ricin-specific single-chain antibodies," IUBMB Life, Nov. 1999, p. 513-p. 517.
Hawkins et al, "Selection of phage antibodies by binding affinity: mimicking affinity maturation," J. MOL. BIOL., Aug. 1992, p. 889-p. 896
Itoh, "Development of Diagnostically and Therapeutically Useful Human Antibody Medicines by Phage Display System," Yakugaku Zasshi, 2007, p. 43-p. 53 .
Office Action in European Patent Application No. 13857248.2, dated Jul. 25, 2018, 8 pages.
Europe Search Report for EP Patent Application No. 13857248.2 dated Apr. 29, 2016.
Hamasaki et al, "Human Anti-Human IL-18 Antibody Recognizing the IL-18-Binding Site 3 with IL-18 Signaling Blocking Activity," Journal of Biochemistry, Oct. 1, 2005, p. 433-p. 442.
Office Action in European Patent Application No. 13857248.2, dated Nov. 8, 2017, 8 pages.
Philippa M. O'Brien and Robert Aitken, "Antibody Phage Display Methods and protocols", Humana Press Methods in Molecular Biology vol. 178 (whole book) (2002).
Adachi O. et al., "Targeted Disruption of the MyD88 Gene Results in Loss of IL-1- and IL-18- Mediated Function", Immunity vol. 9, 1998 , p. 143-p. 150.
Akita, K. et al., "Involvement of Caspase-1 and Caspase-3 in the Production and Processing of Mature Human Interleukin 18 in Monocytic THP.1 Cells", The Journal of Biological Chemistry vol. 272 No. 42, Oct. 17, 1997 , p. 26595-p. 26603.
Arend, W.P. et al., "IL-1, IL-18, and IL-33 families of cytokines.", Immunological. Reviews. vol. 223, Jun. 2008. p. 20-p. 38.
Dinarello, C. A. , "IL-18: A TH1-inducing, proinflammatory cytokine and new member of the IL-1 family", J. Allergy Clin.Immunol vol. 103 No. 1,PART1, Jan. 1999, p. 11-p. 24.
Dinarello, C. A., "Interleukin-18", Methods 19, 1999, p. 121-p. 132.

(Continued)

*Primary Examiner* — Brian Gangle
*Assistant Examiner* — Andrea K McCollum
(74) *Attorney, Agent, or Firm* — Fish & Richardson P.C.

(57) ABSTRACT

The present invention relates to a human anti-human IL-18 antibody which reacts with human interleukin-18 (human IL-18) and does not react with a K53A variant of human IL-18.

17 Claims, 8 Drawing Sheets

Specification includes a Sequence Listing.

(56) References Cited

OTHER PUBLICATIONS

Dinarello, C. et al, "Overview of interleukin-18: more than an interferon-γ inducing factor", Journal of Leukocyte Biology vol. 63, Jun. 1998, p. 658-p. 664.

Fukumoto et al, "Peptide mimics of the CTLA4-binding domain stimulate T-cell proliferation.", Nature Biotechnology vol. 16, No. 3, Mar. 1998, p. 267-p. 270.

Ghayur, T. et al., "Caspase-1 processes IFN-gamma-inducing factor and regulates LPS-induced IFN-gamma production.", Nature., Apr. 10, 1997, p. 619-p. 623.

Gracie J. A. et al., "Interleukin-18", Journal of Leukocyte Biology vol. 73, Feb. 2003, p. 213-p. 224.

Gu.Y, et al., "Activation of interferon-gamma inducing factor mediated by interleukin-1beta converting enzyme.", Science vol. 275, Jan. 10, 1997, p. 206-p. 209.

Hamasaki, T. et al., "Human anti-human IL-18 antibody recognizing the IL-18-binding site 3 with IL-18 signaling blocking activity", Journal of Biochemistry vol. 138, No. 4, Oct. 2005, p. 433-p. 442.

Hoshino K. et al, "Cutting Edge: Generation of IL-18 Receptor-Deficient Mice: Evidence for IL-1 Receptor-Related Protein as an Essential IL-18 Binding Receptor", The Journal of Immunology, 1999, p. 5041-p. 5044.

Hoshino,T.et al., "Role of proinflammatory cytokines IL-18 and IL-1beta in bleomycin-induced lung injury in humans and mice.", American Journal of Respiratory Cell Molecular Biology.vol. 41, 2009, p. 661-p. 670.

Imaoka, H.et al., "Interleukin-18 production and pulmonary function in COPD", Eur. Respir J vol. 31, 2008, p. 287-p. 297.

International Preliminary Report on Patentability and Written Opinion for PCT/JP2013/081057 dated May 26, 2015.

International Search Report for PCT/JP12013/081057 dated Feb. 4, 2014.

KanakarajP. et al., "Defective Interleukin (IL)-18—mediated Natural Killer and T Helper Cell Type 1 Responses in IL-1 Receptor—associated Kinase (IRAK)-deficient Mice", J. Exp. Med.vol. 189 No. 7, Apr. 5, 1999, p. 1129-p. 1138.

Kawaguchi,Y. et al., "Interleukin-18 as a novel diagnostic marker and indicator of disease severity in adult-onset Still's disease", Arthritis Rheum vol. 44 No. 7, Jul. 2001, p. 1716-p. 1717.

Kimura T,.et al, "Expression, purification and structural analysis of human IL-18 binding protein: a potent therapeutic molecule for allergy.", Allergology International vol. 57 No. 4, 2008, p. 367-p. 376.

Konishi, H. et al., "IL-18 contributes to the spontaneous development of atopic dermatitis-like inflammatory skin lesion independently of IgE stat6 under specific pathogen-free conditions", *PNAS*, USA vol. 99 No. 17, Aug. 20, 2002, p. 11340-p. 11345.

Krumm, B. et al., "A unique bivalent binding and inhibition mechanism by the yatapoxvirus interleukin 18 binding protein", PLOS Pathogens vol. 8, No. 8, Aug. 2012, e1002876, p. 1-p. 15.

Lei, SP. et al. , "Characterization of the Erwinia carotovora pelB Gene and Its Product Pectate Lyase", Journal of Bacteriology vol. 169 No. 9, Sep. 1987, p. 4379-p. 4383.

Li, A. et al., "Optimized gene synthesis and high expression of human interleukin-18.", Protein Expression and Purification 32, 2003, p. 110-p. 118.

McInnes. B.et. al. , "Interleukin 18: a pleiotropic participant in chronic inflammation", Immunology Today vol. 21, No. 7, Jul. 2000, p. 312-p. 315 .

Melnikov, V.Y. et al., "Impaired IL-18 processing protects caspase-1—deficient mice from ischemic acute renal failure", The Journal of Clinical Investigation vol. 107 No. 9, May 2001 , p. 1145-p. 1152.

Meng, X. et al., "Variola virus IL-18 binding protein interacts with three human IL-18 residues that are part of a binding site for human IL-18 receptor alpha subunit", Virology vol. 358, No. 1, Feb. 5, 2007, p. 211-p. 220.

Nakanishi,K. et al, "Interleukin-18 regulates both Th1 and Th2 responses.", Annual Review of Immunology.vol. 19, 2001, p. 423-p. 474.

Novick, D. et al., "Interleukin-18 Binding Protein: A Novel Modulator of the Th1 Cytokine Response", Immunity vol. 10, 1999 , p. 127-p. 136.

Okamoto M. et al., "Interleukin 18 (IL-18) in synergy with IL-2 induces lethal lung injury in mice: a potential role for cytokines, chemokines, and natural killer cells in the pathogenesis of interstitial pneumonia", Blood vol. 99 No. 4, Feb. 15, 2002 , p. 1289-p. 1298.

Omoto, Y. et al, "Human Mast Cell Chymase Cleaves Pro-IL-18 and Generates a Novel and Biologically Active IL-18 Fragment", The Journal of Immunology, 2006, p. 8315-p. 8319.

Sims, J.E., "IL-1 and IL-18 receptors, and their extended family.", Current Opinion in Immunology.vol. 14 No. 1, Feb. 2002, p. 117-p. 122.

Sugawara, S. et al, "Neutrophil Proteinase 3-Mediated Induction of Bioactive IL-18 Secretion by Human Oral Epithelial Cells", The Journal of Immunology, 2001, p. 6568-p. 6575.

Tak PP. et al., "Pharmacokinetics of IL-18 binding protein in healthy volunteers and subjects with rheumatoid arthritis or plaque psoriasis.", European Journal of Drug Metabolism and Pharmacokinetics vol. 31 No. 2, 2006, p. 109-p. 116.

Tsutsui, H. et al, "Caspase-1-Independent, Fas/Fas Ligand—Mediated IL-18 Secretion from Macrophages Causes Acute Liver Injury in Mice", Immunity vol. 11, Sep., 1999 , p. 359-p. 367.

* cited by examiner

SEQUENCE LISTING

```
<160> NUMBER OF SEQ ID NOS: 12

<210> SEQ ID NO 1
<211> LENGTH: 747
<212> TYPE: DNA
<213> ORGANISM: Homo sapiens

<400> SEQUENCE: 1 gag gtg cag ctg gtg gag tct ggg gga ggc ttg gtc cag cct ggg ggg      48
Glu Val Gln Leu Val Glu Ser Gly Gly Gly Leu Val Gln Pro Gly Gly
1               5                   10                  15 tcc atg aga ctc tcc tgt acc gcc tct gga ttc acc ttt gac gaa tat      96
```

-continued

```
                Ser Met Arg Leu Ser Cys Thr Ala Ser Gly Phe Thr Phe Asp Glu Tyr
                             20                  25                  30 gcc atg agc tgg gtc cgc cag gct cca ggg aag ggg ctg gag tgg gtc        144
Ala Met Ser Trp Val Arg Gln Ala Pro Gly Lys Gly Leu Glu Trp Val
             35                  40                  45 tca ggt att agt act ggt ggt ggt ggc aca tac tac gca gac tcc gtg        192
Ser Gly Ile Ser Thr Gly Gly Gly Gly Thr Tyr Tyr Ala Asp Ser Val
 50                  55                  60 gag ggc cgg ttc acc atc tcc aga gac aat tcc aag aac aca ctg tat        240
Glu Gly Arg Phe Thr Ile Ser Arg Asp Asn Ser Lys Asn Thr Leu Tyr
 65                  70                  75                  80 ctg caa atg aac agc ctg aga gcc gag gac acg gcc gta tac tac tgt        288
Leu Gln Met Asn Ser Leu Arg Ala Glu Asp Thr Ala Val Tyr Tyr Cys
                 85                  90                  95 gcg aaa ccc tgg ctc tct ggt tcg agg agt ggg gac ttc tgg ggc cag        336
Ala Lys Pro Trp Leu Ser Gly Ser Arg Ser Gly Asp Phe Trp Gly Gln
            100                 105                 110 gga acc ctg gtc acc gtc tcc tca gct agc acc ggc gga ggc ggt agt        384
Gly Thr Leu Val Thr Val Ser Ser Ala Ser Thr Gly Gly Gly Gly Ser
            115                 120                 125 gga ggc ggt gga tct gga ggc ggt ggc tcg caa tct gcc ctg act cag        432
Gly Gly Gly Gly Ser Gly Gly Gly Gly Ser Gln Ser Ala Leu Thr Gln
            130                 135                 140 cct gcc tcc gtg tct ggg tct cct ggg cag tcg atc acc atc tcc tgc        480
Pro Ala Ser Val Ser Gly Ser Pro Gly Gln Ser Ile Thr Ile Ser Cys
145                 150                 155                 160 act gga acc agc agt gac gtt ggt ggt tat aac tat gtc tcc tgg tac        528
Thr Gly Thr Ser Ser Asp Val Gly Gly Tyr Asn Tyr Val Ser Trp Tyr
                165                 170                 175 caa cag cac cca ggc aaa gcc ccc aaa ctc ttg att tat gag gtc agt        576
Gln Gln His Pro Gly Lys Ala Pro Lys Leu Leu Ile Tyr Glu Val Ser
            180                 185                 190 cat cgg ccc tca ggg gtt tct gac cgc ttc tct ggc tcc aag tct ggc        624
His Arg Pro Ser Gly Val Ser Asp Arg Phe Ser Gly Ser Lys Ser Gly
            195                 200                 205 aac acg gcc tcc ctg acc atc tct ggg ctc cag gct gag gac gag gct        672
Asn Thr Ala Ser Leu Thr Ile Ser Gly Leu Gln Ala Glu Asp Glu Ala
            210                 215                 220 gat tat tat tgt agc tca ttt act agc agt agc tct ctc tat gtc ttc        720
Asp Tyr Tyr Cys Ser Ser Phe Thr Ser Ser Ser Leu Tyr Val Phe
225                 230                 235                 240 gga act ggg acc aag ctg acc gtc cta                                    747
Gly Thr Gly Thr Lys Leu Thr Val Leu
                245

<210> SEQ ID NO 2
<211> LENGTH: 747
<212> TYPE: DNA
<213> ORGANISM: Homo sapiens

<400> SEQUENCE: 2 gag gtg cag ctg gtg gag tct ggg gga ggc ttg gtc cag cct ggg ggg         48
Glu Val Gln Leu Val Glu Ser Gly Gly Gly Leu Val Gln Pro Gly Gly
 1               5                  10                  15 tcc atg aga ctc tcc tgt acc gcc tct gga ttc acc ttt agc gaa tat         96
Ser Met Arg Leu Ser Cys Thr Ala Ser Gly Phe Thr Phe Ser Glu Tyr
             20                  25                  30 gcc atg agc tgg gtc cgc cag gct cca ggg aag ggg ctg gag tgg gtc        144
Ala Met Ser Trp Val Arg Gln Ala Pro Gly Lys Gly Leu Glu Trp Val
             35                  40                  45
```

| | | |
|---|---|---|
| tca ggt att agt act ggt ggt ggt ggc aca tac tac gca gac tcc gtg<br>Ser Gly Ile Ser Thr Gly Gly Gly Gly Thr Tyr Tyr Ala Asp Ser Val<br>50                            55                          60 | | 192 |
| gag ggc cgg ttc acc atc tcc aga gac aat tcc aag aac aca ctg tat<br>Glu Gly Arg Phe Thr Ile Ser Arg Asp Asn Ser Lys Asn Thr Leu Tyr<br>65                            70                          75                        80 | | 240 |
| ctg caa atg aac agc ctg aga gcc gag gac acg gcc gta tac tac tgt<br>Leu Gln Met Asn Ser Leu Arg Ala Glu Asp Thr Ala Val Tyr Tyr Cys<br>                            85                          90                        95 | | 288 |
| gcg aaa ccc tgg ctc tct ggt tcg agg agt ggg gac ttc tgg ggc cag<br>Ala Lys Pro Trp Leu Ser Gly Ser Arg Ser Gly Asp Phe Trp Gly Gln<br>                      100                        105                     110 | | 336 |
| gga acc ctg gtc acc gtc tcc tca gct agc acc ggc gga ggc ggt agt<br>Gly Thr Leu Val Thr Val Ser Ser Ala Ser Thr Gly Gly Gly Gly Ser<br>             115                       120                     125 | | 384 |
| gga ggc ggt gga tct gga ggc ggt ggc tcg caa tct gcc ctg act cag<br>Gly Gly Gly Gly Ser Gly Gly Gly Gly Ser Gln Ser Ala Leu Thr Gln<br>130                           135                        140 | | 432 |
| cct gcc tcc gtg tct ggg tct cct ggg cag tcg atc acc atc tcc tgc<br>Pro Ala Ser Val Ser Gly Ser Pro Gly Gln Ser Ile Thr Ile Ser Cys<br>145                          150                        155                        160 | | 480 |
| act gga acc agc agt gac gtt ggt ggt tat aac tat gtc tcc tgg tac<br>Thr Gly Thr Ser Ser Asp Val Gly Gly Tyr Asn Tyr Val Ser Trp Tyr<br>                      165                        170                     175 | | 528 |
| caa cag cac cca ggc aaa gcc ccc aaa ctc ttg att tat gag gtc agt<br>Gln Gln His Pro Gly Lys Ala Pro Lys Leu Leu Ile Tyr Glu Val Ser<br>             180                       185                     190 | | 576 |
| cat cgg ccc tca ggg gtt tct gac cgc ttc tct ggc tcc aag tct ggc<br>His Arg Pro Ser Gly Val Ser Asp Arg Phe Ser Gly Ser Lys Ser Gly<br>         195                        200                     205 | | 624 |
| aac acg gcc tcc ctg acc atc tct ggg ctc cag gct gag gac gag gct<br>Asn Thr Ala Ser Leu Thr Ile Ser Gly Leu Gln Ala Glu Asp Glu Ala<br>210                           215                        220 | | 672 |
| gat tat tat tgt agc tca ttt act agc agt agc tct ctc tat gtc ttc<br>Asp Tyr Tyr Cys Ser Ser Phe Thr Ser Ser Ser Ser Leu Tyr Val Phe<br>225                          230                        235                        240 | | 720 |
| gga act ggg acc aag ctg acc gtc cta<br>Gly Thr Gly Thr Lys Leu Thr Val Leu<br>             245 | | 747 |

<210> SEQ ID NO 3
<211> LENGTH: 120
<212> TYPE: PRT
<213> ORGANISM: Homo sapiens

<400> SEQUENCE: 3

Glu Val Gln Leu Val Glu Ser Gly Gly Leu Val Gln Pro Gly Gly
1               5                   10                  15

Ser Met Arg Leu Ser Cys Thr Ala Ser Gly Phe Thr Phe Asp Glu Tyr
            20                  25                  30

Ala Met Ser Trp Val Arg Gln Ala Pro Gly Lys Gly Leu Glu Trp Val
        35                  40                  45

Ser Gly Ile Ser Thr Gly Gly Gly Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Trp Leu Ser Gly Ser Arg Ser Gly Asp Phe Trp Gly Gln

```
                100                 105                 110
Gly Thr Leu Val Thr Val Ser Ser
            115                 120

<210> SEQ ID NO 4
<211> LENGTH: 111
<212> TYPE: PRT
<213> ORGANISM: Homo sapiens

<400> SEQUENCE: 4

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Glu Val Ser His Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Ser Ser
                85                  90                  95

Ser Ser Leu Tyr Val Phe Gly Thr Gly Thr Lys Leu Thr Val Leu
            100                 105                 110

<210> SEQ ID NO 5
<211> LENGTH: 120
<212> TYPE: PRT
<213> ORGANISM: Homo sapiens

<400> SEQUENCE: 5

Glu Val Gln Leu Val Glu Ser Gly Gly Gly Leu Val Gln Pro Gly Gly
1               5                   10                  15

Ser Met Arg Leu Ser Cys Thr Ala Ser Gly Phe Thr Phe Ser Glu Tyr
            20                  25                  30

Ala Met Ser Trp Val Arg Gln Ala Pro Gly Lys Gly Leu Glu Trp Val
        35                  40                  45

Ser Gly Ile Ser Thr Gly Gly Gly Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Trp Leu Ser Gly Ser Arg Ser Gly Asp Phe Trp Gly Gln
            100                 105                 110

Gly Thr Leu Val Thr Val Ser Ser
            115                 120

<210> SEQ ID NO 6
<211> LENGTH: 111
<212> TYPE: PRT
<213> ORGANISM: Homo sapiens

<400> SEQUENCE: 6

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30
```

```
Asn Tyr Val Ser Trp Tyr Gln Gln His Pro Gly Lys Ala Pro Lys Leu
            35                  40                  45

Leu Ile Tyr Glu Val Ser His Arg Pro Ser Gly Val Ser Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Phe Thr Ser Ser
                 85                  90                  95

Ser Ser Leu Tyr Val Phe Gly Thr Gly Thr Lys Leu Thr Val Leu
            100                 105                 110
```

```
<210> SEQ ID NO 7
<211> LENGTH: 5
<212> TYPE: PRT
<213> ORGANISM: Homo sapiens

<400> SEQUENCE: 7

Glu Tyr Ala Met Ser
1               5

<210> SEQ ID NO 8
<211> LENGTH: 17
<212> TYPE: PRT
<213> ORGANISM: Homo sapiens

<400> SEQUENCE: 8

Gly Ile Ser Thr Gly Gly Gly Thr Tyr Tyr Ala Asp Ser Val Glu
1               5                   10                  15

Gly

<210> SEQ ID NO 9
<211> LENGTH: 11
<212> TYPE: PRT
<213> ORGANISM: Homo sapiens

<400> SEQUENCE: 9

Pro Trp Leu Ser Gly Ser Arg Ser Gly Asp Phe
1               5                   10

<210> SEQ ID NO 10
<211> LENGTH: 14
<212> TYPE: PRT
<213> ORGANISM: Homo sapiens

<400> SEQUENCE: 10

Thr Gly Thr Ser Ser Asp Val Gly Gly Tyr Asn Tyr Val Ser
1               5                   10

<210> SEQ ID NO 11
<211> LENGTH: 7
<212> TYPE: PRT
<213> ORGANISM: Homo sapiens

<400> SEQUENCE: 11

Glu Val Ser His Arg Pro Ser
1               5

<210> SEQ ID NO 12
<211> LENGTH: 11
<212> TYPE: PRT
<213> ORGANISM: Homo sapiens
```

```
<400> SEQUENCE: 12

Ser Ser Phe Thr Ser Ser Ser Ser Leu Tyr Val
1               5                   10
```

HUMAN ANTIBODY AGAINST IL-18

SEQUENCE LISTING

The instant application contains a Sequence Listing which has been submitted electronically in ASCII format and is hereby incorporated by reference in its entirety. Said ASCII copy, created on Jul. 13, 2015, is named SeqList.txt and is 12,600 bytes in size.

TECHNICAL FIELD

The present invention relates to a human anti-human IL-18 antibody which binds to human interleukin-18 (hereinafter, referred to as "human IL-18") and inhibits its biological activity and an antibody fragment thereof, and methods for using the same. The antibody and the antibody fragment are useful in the diagnosis and treatment of a disease caused by IL-18.

BACKGROUND ART

In 1989, interleukin-18 (IL-18) was regarded as interferon-γ (IFN-γ)-inducing factor (IGIF). Now, it is known that IL-18 is a proinflammatory cytokine having various functions in addition to the ability to induce interferon-γ. IL-18 has functions such as activation of NF-κB, expression of Fas ligand, induction of both CC and CXC chemokines, and increase in the production of competent human immunodeficiency virus. Since IL-18 has the ability to induce interferon-γ production in T cells and macrophages, it plays an important role in Th1-type immune response and participates both in congenital immunity and in acquired immunity. IL-18 is related to the IL-1 family both in terms of structures and in terms of functions. Reviews regarding the structure, functions, and biological activity of IL-18 have been made (e.g., Non Patent Literatures 1 to 5).

Intracellular pro-IL-18 is treated in a proteolytic manner by caspase 1 in endotoxin-stimulated cells (Non Patent Literatures 6 and 7) as well as by caspases 4, 5, and 6 in Fas-L or bacterial DNA-stimulated cells (Non Patent Literature 8) to become a 18 kDa active form. Pro-IL-18 is also activated in a proteolytic manner by other proteases including mast cell-derived chymase (Non Patent Literature 9), neutrophil proteinase 3 (Non Patent Literature 10), caspase 3 (Non Patent Literature 11), and elastase and cathepsin (Non Patent Literature 12), which are serine proteases. IL-18 in both humans and mice lacks a leader sequence, and the mechanism underlying mature IL-18 release from cells has not yet been elucidated sufficiently.

The biological activity of IL-18 is mediated by the binding of IL-18 to heterodimer IL-18 receptor (IL-18R) consisting of two subunits: α-subunit (one member of the IL-1R family also called IL-1R-related protein-1 or IL-1Rrp1) and β-subunit (also called IL-18R accessory protein, IL-18AP, or AcPL). The IL-18R α-subunit binds directly to IL-18, but cannot induce signal transduction. The IL-18R β-subunit does not bind to IL-18 in itself, but forms a high-affinity receptor (KD=approximately 0.3 nM) necessary for signal transduction, in collaboration with the α-subunit (Non Patent Literature 13). The IL-18 signal transduction mediated by the IL-18R αβ complex is similar to that of the IL-1R and toll-like receptor (TLR) system. The IL-18R signal transduction employs signal transduction molecules such as MyD88, IRAK, and TRAF6 to cause responses as in the case of IL-1, for example, activation of NIK, IκB kinase, NF-κB, JNK, and p38MAP kinase. It has been confirmed using IL-18Rα subunit (Non Patent Literature 14) and MyD88 (Non Patent Literature 15) or IRAK (Non Patent Literature 16) knockout variants that IL-18Rα and the signal transduction molecules, respectively, are necessary for the biological activity exhibition of IL-18.

Interstitial pneumonia (Non Patent Literature 17), adult-onset Still's disease (Non Patent Literature 18), chronic obstructive pulmonary disease (Non Patent Literature 19), metabolic bone disease (Patent Literature 1), multiple sclerosis (Non Patent Literature 5), diabetes mellitus (Non Patent Literature 5), ischemic kidney damage (Non Patent Literature 20), and the like have previously been reported as diseases with the overexpression of IL-18. Also, the overexpression of IL-18 is responsible for so-called Th1 diseases such as atopic dermatitis (Non Patent Literature 21) and serious organ damages in the liver and the intestine (Non Patent Literature 5).

In addition to these diseases, the involvement of IL-18 in the pathological conditions of bronchial asthma induced by Th1 cells and other various diseases has been pointed out.

The control of production or activity of IL-18 is very important as a therapy for such IL-18-dependent diseases or as a therapy for diseases whose onset is induced or which are exacerbated due to the excessive production of IL-18.

CITATION LIST

Patent Literature

Patent Literature 1: U.S. Patent Application Publication No. 2005074434
Patent Literature 2: U.S. Patent Application Publication No. 20050100965
Patent Literature 3: U.S. Patent Application Publication No. 20070292432
Patent Literature 4: U.S. Pat. No. 6,706,487
Patent Literature 5: International Publication No. WO 2004/097019

Non Patent Literature

Non Patent Literature 1: Dinarello, C. Et al. (1998) J. Leukoc. Biol. 63: 658-664
Non Patent Literature 2: Dinarello, C. A. (1999) Methods 19: 121-132
Non Patent Literature 3: Dinarello, C. A. (1999) J. Allergy Clin. Immunol. 103: 11-24
Non Patent Literature 4: McInnes. B. et al. (2000) Immunology Today 21: 312-315
Non Patent Literature 5: Nakanishi, K. et al (2001) Ann. Rev. Immunol. 19: 423-474
Non Patent Literature 6: Ghayur, T. et al. (1997) Nature 386: 619-623
Non Patent Literature 7: Gu, et al. (1997) Science 275: 206-209
Non Patent Literature 8: Tsutsui, H. et al. (1999) Immunity 11: 359-67
Non Patent Literature 9: Omoto, Y. et al. (2006) J. Immunol. 177: 8315-8319
Non Patent Literature 10: Sugawara, S. et al. (2001) J. Immunol. 167: 6568-6575
Non Patent Literature 11: Akita, K. et al. (1997) J. Biol. Chem. 272: 26595-26603
Non Patent Literature 12: Gracie J. A. et al. (2003) Journal of Leukocyte Biology 73: 213-224
Non Patent Literature 13: Sims, J. E. et al (2002) Current Opin. Immunol. 14: 117-122

Non Patent Literature 14: Hoshino K. et al (1999) J. Immunol. 162: 5041-5044

Non Patent Literature 15: Adachi O. et al. (1998) Immunity 9: 143-150

Non Patent Literature 16: Kanakaraj P. et al. (1999) J. Exp. Med. 189: 1129-1138

Non Patent Literature 17: Hoshino, T. et al. (2009) Am. J. Respir. Cell Mol. Biol. 41: 661-670

Non Patent Literature 18: Kawaguchi, Y. et al. (2001) Arthritis Rheum. 44: 1716-1717

Non Patent Literature 19: Imaoka, H. et al. (2008) Eur. Respir. J. 31: 287-297

Non Patent Literature 20: Melnikov, V. Y. et al. (2001) J. Clin. Invest. 107: 1145-1152

Non Patent Literature 21: Konishi, H. et al. (2002) Proc. Natl. Acad. Sci. USA 99: 11340-11345

Non Patent Literature 22: Novick, D. et al. (1999) Immunity 10: 127-136

Non Patent Literature 23: Arend, W. P. et al. (2008) Immunol. Rev. 223: 20-38

Non Patent Literature 24: Tak P. et al. (2006) Eur. J. Drug Metab. Pharmacokinet. 31: 109-116

Non Patent Literature 25: Lei, S P. et al. (1987) J. Bacteriol. 169: 4379-4383

Non Patent Literature 26: T. Fukumoto et al. (1998) Nature Biotechnology 16: 267-270

Non Patent Literature 27: Okamoto M. et al. (2002) Blood 99: 1289-98

Non Patent Literature 28: Antibody Phage Display Methods and protocols Edited by Philippa M. O'Brien and Robert Aitken Non Patent Literature 29: Kimura T. et al. (2008) Allergology International 57: 367-376

Non Patent Literature 30: Hamasaki T. et al. (2005) J. Biochem. 138: 433-442

Non Patent Literature 31: Li, A. et al. (2003) Protein Expr Purif. 32:110-118

SUMMARY OF INVENTION

Problems to be Solved by the Invention

It is known that a protein that binds to IL-18, called IL-18-binding protein (IL-18BP), is present in human bodies. IL-18BP binds to IL-18, thereby inhibiting the binding between IL-18 and IL-18 receptor and regulating the activity (Non Patent Literature 22). In the case of human IL-18BP, four isoforms (IL-18BPa, IL-18BPb, IL-18BPc, and IL-18BPd) obtained by the splicing of mRNA are present (Non Patent Literature 23). Of them, one having the highest affinity for IL-18 is IL-18BPa, and its neutralizing ability ($IC_{50}$) is reportedly on the order of 0.4 nM. IL-18BP also has the feature that it does not bind to precursor IL-18, which lacks activity, but binds to mature-form (active-form) IL-18. The IL-18BP concentrations in blood of healthy humans are reportedly 0.5 to 0.7 ng/mL, and IL-18BP inhibits the activity of a trace amount of mature-form IL-18 present in blood.

From these, it is proposed that IL-18BP, which is originally present in vivo, also safe as a therapeutic drug, and has a definite working mechanism for IL-18, is used as a therapeutic agent for the diseases mentioned above. However, IL-18BP has been susceptible to improvement in, for example, the need of frequent administration for maintaining the efficacy, because the half-life in blood is as short as 34 to 40 hours (Non Patent Literature 24).

Hence, if a specific monoclonal antibody that neutralizes the biological activity of IL-18 under a mechanism closer to that in vivo can be developed, it is expected to become a safer and more effective therapeutic approach for diseases in which IL-18 is involved, i.e., diseases associated with change in the expression level of IL-18.

Against this backdrop, although a plurality of IL-18 activity inhibitors have been obtained so far, it has been shown that they do not bind to the same site as a site of IL-18 to which IL-18BP binds (IL-18BP recognition region), and do not have an inhibitory mechanism similar to that of IL-18BP (Patent Literatures 2 and 3). This means that, in screening for IL-18 inhibitors, it is difficult to expose IL-18BP recognition region present in IL-18 and maintain it, and consequently means that the obtainment of IL-18 activity inhibitors based on an inhibitory mechanism similar to that of IL-18BP is very difficult.

In light of the problems mentioned above, the present invention has achieved the production of a longer acting IL-18 activity inhibitor than IL-18BP by using an antibody molecule that has an inhibitory mechanism similar to that of the in vivo natural IL-18 activity inhibitor IL-18BP (i.e., binds to the same site as the IL-18BP recognition region), is safer, and has a longer half-life in blood.

Means for Solving the Problems

The present inventors have conducted diligent studies in light of the problems mentioned above and consequently completed the present invention. A target protein (in this case, IL-18) usually used in antibody screening (panning) from a phage display library is typically immobilized directly onto an ELISA plate. In contrast to this, the present inventors have variously studied conditions for panning, such as panning in liquid-phase methods and solid-phase methods that control the orientation or conformation of IL-18 via various existing anti-IL-18 antibodies.

As a result, the present inventors have succeeded in exposing the IL-18BP recognition region and displaying IL-18 that maintains the exposed state.

The present inventors have also succeeded in obtaining a single-chain variable fragment (scFv) of a desired complete human anti-human IL-18 antibody from a phage display library expressing genes encoding variable regions (VH and VL) of an immunoglobulin H chain and L chain prepared from the peripheral blood B lymphocytes of a healthy person.

The present inventors have further found that this antibody fragment and an antibody prepared on the basis of the fragment inhibit the biological activity of human IL-18.

Specifically, the present invention includes the following aspects as medically or industrially useful methods and substances:

[1] A human anti-human IL-18 antibody which reacts with human interleukin-18 (human IL-18) and does not react with a K53A variant of human IL-18.

[2] A human anti-human IL-18 antibody which reacts with human IL-18 and does not react with a complex of human IL-18 and human IL-18 BP.

[3] The antibody according to [1] or [2], wherein complementarity determining region (CDR)1 of an H chain consists of the amino acid sequence of SEQ ID NO: 7 or an amino acid sequence in which one or several amino acids in the amino acid sequence of SEQ ID NO: 7 are deleted, substituted, or added, CDR2 of the H chain consists of the amino acid sequence of SEQ ID NO: 8 or an amino acid sequence in which one or several amino acids in the amino acid sequence of SEQ ID NO: 8 are deleted, substituted, or added, CDR3 of the H chain consists of the amino acid sequence of SEQ ID NO: 9 or an amino acid sequence in which one or several amino acids in the amino acid sequence of SEQ ID NO: 9 are deleted, substituted, or added, CDR1 of an L chain consists of the amino acid sequence of SEQ ID NO: 10 or an amino acid sequence in which one or several amino acids in the amino acid sequence of SEQ ID NO: 10 are deleted, substituted, or added, CDR2 of the L chain consists of the amino acid sequence of SEQ ID NO: 11 or an amino acid sequence in which one or several amino acids in the amino acid sequence of SEQ ID NO: 11 are deleted, substituted, or added, and CDR3 of the L chain consists of the amino acid sequence of SEQ ID NO: 12 or an amino acid sequence in which one or several amino acids in the amino acid sequence of SEQ ID NO: 12 are deleted, substituted, or added.

[4] The antibody according to any of [1] to [3], wherein an H chain variable region consists of an amino acid sequence of SEQ ID NO: 3 or 5 or an amino acid sequence in which one or several amino acids in the amino acid sequence of SEQ ID NO: 3 or 5 are deleted, substituted, or added, and an L chain variable region consists of an amino acid sequence of SEQ ID NO: 4 or 6 or an amino acid sequence in which one or several amino acids in the amino acid sequence of SEQ ID NO: 4 or 6 are deleted, substituted, or added.

[5] An H chain variable region fragment consisting of an amino acid sequence of SEQ ID NO: 3 or 5 or an amino acid sequence in which one or several amino acids in the amino acid sequence of SEQ ID NO: 3 or 5 are deleted, substituted, or added, wherein the H chain variable region fragment reacts with human IL-18 and does not react with a K53A variant of human IL-18 or a complex of human IL-18 and human IL-18 BP.

[6] An L chain variable region fragment consisting of an amino acid sequence of SEQ ID NO: 4 or 6 or an amino acid sequence in which one or several amino acids in the amino acid sequence of SEQ ID NO: 4 or 6 are deleted, substituted, or added, wherein the L chain variable region fragment reacts with human IL-18 and does not react with a K53A variant of human IL-18 or a complex of human IL-18 and human IL-18 BP.

[7] A single-chain variable region fragment of a human anti-human IL-18 antibody, wherein the H chain variable region fragment of the antibody according to [3] or the H chain variable region fragment according to [5] is linked to the L chain variable region fragment of the antibody according to [3] or the L chain variable region fragment according to [6].

[8] A human anti-human IL-18 antibody, wherein a constant region of a human-derived antibody is linked to the H chain variable region fragment of the antibody according to [3] or the H chain variable region fragment according to [5] and/or the L chain variable region fragment of the antibody according to [3] or the L chain variable region fragment according to [6].

[9] A fragment of the antibody according to [8].

[10] The fragment according to [9], wherein the fragment is Fab, Fab', F(ab')2, scAb, or scFvFc.

[11] A modified antibody, wherein a modifier is bound to the antibody according to any of [1] to [4] and [8] or the fragment according to any of [5] to [7], [9], and [10].

[12] A gene encoding the antibody according to any of [1] to [4] and [8] or the fragment according to any of [5] to [7], [9], and [10].

[13] The gene according to [12], wherein the gene has a gene encoding an amino acid sequence of any of SEQ ID NOs: 3 to 6 as an open reading frame region.

[14] A recombinant expression vector comprising the gene according to [12] or [13].

[15] A transformant in which the gene according to [12] or [13] is introduced.

[16] A method for producing the antibody according to any of [1] to [4] and [8] or the fragment according to any of [5] to [7], [9], and [10], comprising allowing a host to express the gene according to [12] or [13].

[17] A detection apparatus for human IL-18 comprising the antibody according to any of [1] to [4] and [8], the fragment according to any of [5] to [7], [9], and [10], or the modified antibody according to [11].

[18] A diagnostic kit for a disease associated with change in the expression level of IL-18, comprising a human IL-18 detection reagent consisting of the antibody according to any of [1] to [4] and [8], the fragment according to any of [5] to [7], [9], and [10], or the modified antibody according to [11].

[19] The diagnostic kit according to [18], wherein the disease is hyper-IL-18-naemia in a human.

[20] The diagnostic kit according to [18] or [19], wherein the disease is selected from the group consisting of allergy, inflammation, and chronic immune disorder.

[21] The diagnostic kit according to any of [18] to [20], wherein the disease is selected from the group consisting of interstitial pneumonia, adult-onset Still's disease, chronic obstructive pulmonary disease, metabolic bone disease, multiple sclerosis, diabetes mellitus, atopic dermatitis, airway inflammation, airway hyperresponsiveness (AHR), asthma, and serious organ damages in the liver, the kidney, and the intestine.

[22] A method for diagnosing a disease on the basis of a human IL-18 level in a test sample measured using the diagnostic kit according to any of [18] to [21].

[23] A human IL-18 activity inhibitor containing the antibody according to any of [1] to [4] and [8], the fragment according to any of [5] to [7], [9], and [10], or the modified antibody according to [11] as an active ingredient.

[24] A human IL-18 binding inhibitor containing the antibody according to any of [1] to [4] and [8], the fragment according to any of [5] to [7], [9], and [10], or the modified antibody according to [11] as an active ingredient, wherein the human IL-18 binding inhibitor inhibits the binding between human IL-18 and human IL-18 receptor.

[25] An interferon-γ production inhibitor containing the antibody according to any of [1] to [4] and [8], the fragment according to any of [5] to [7], [9], and [10], or the modified antibody according to [11] as an active ingredient.

[26] A gene therapeutic agent comprising the gene according to [12] or [13].

[27] A therapeutic agent for an IL-18-associated disease, comprising the human IL-18 activity inhibitor according to [23], the human IL-18 binding inhibitor according to [24], the interferon-γ production inhibitor according to [25], or the gene therapeutic agent according to [26].

[28] The therapeutic agent according to [27], wherein the disease is hyper-IL-18-naemia in a human.

[29] The therapeutic agent according to [27] or [28], wherein the disease is selected from the group consisting of allergy, inflammation, and chronic immune disorder.

[30] The therapeutic agent according to any of [27] to [29], wherein the disease is selected from the group consisting of interstitial pneumonia, adult-onset Still's disease, chronic obstructive pulmonary disease, metabolic bone disease, multiple sclerosis, diabetes mellitus, atopic dermatitis, airway inflammation, airway hyperresponsiveness (AHR), asthma, and serious organ damages in the liver, the kidney, and the intestine.

[31] The therapeutic agent according to any of [27] to [30], for use in inhibition of the binding between human IL-18 and human IL-18 receptor.

[32] The therapeutic agent according to any of [27] to [31], for use in inhibition of interferon-γ production from a helper T1 cell.

[33] A method for treating an IL-18-associated disease, comprising administering the therapeutic agent according to any of [27] to [32].

[34] A method for preparing the antibody according to any of [1] to [4] and [8] or the fragment according to any of [5] to [7], [9], and [10], comprising binding human IL-18 to a support in the form of beads via a linker and then reacting the support with a phage display library under conditions that expose and maintain an IL-18BP recognition region of the human IL-18.

[35] A human anti-human IL-18 antibody binding to the same site as a human IL-18BP recognition region.

[36] The antibody according to [35], wherein the antibody inhibits human IL-18 activity.

[37] The antibody according to [35] or [36], wherein the antibody inhibits the binding between human IL-18 and human IL-18 receptor.

[38] The antibody according to any of [35] to [37], wherein the antibody inhibits interferon-γ (IFN-γ) production.

[39] The antibody according to any of [35] to [38], wherein an epitope is a region comprising lysine at the position 53 of human IL-18.

[40] The antibody according to any of [35] to [39], wherein the antibody comprises complementarity determining regions of an H chain consisting of polypeptides of the following (a) or (b) and complementarity determining regions of an L chain consisting of polypeptides of the following (c) or (d):

(a) polypeptides consisting of the amino acid sequences shown in SEQ ID NOs: 7 to 9, (b) polypeptides which consist of amino acid sequences in which one or several amino acids in the amino acid sequences shown in SEQ ID NOs: 7 to 9 are substituted, deleted, inserted, and/or added, and serve as complementarity determining regions of an H chain against human IL-18, (c) polypeptides consisting of the amino acid sequences shown in SEQ ID NOs: 10 to 12, and (d) polypeptides which consist of amino acid sequences in which one or several amino acids in the amino acid sequences shown in SEQ ID NOs: 10 to 12 are substituted, deleted, inserted, and/or added, and serve as complementarity determining regions of an L chain against human IL-18.

[41] The human anti-human IL-18 antibody according to [40], wherein the antibody comprises an H chain variable region consisting of a polypeptide of the following (e) or (f) and an L chain variable region consisting of a polypeptide of the following (g) or (h):

(e) a polypeptide consisting of an amino acid sequence shown in SEQ ID NO: 3 or 5, (f) a polypeptide which consists of an amino acid sequence in which one or several amino acids in the amino acid sequence shown in SEQ ID NO: 3 or 5 are substituted, deleted, inserted, and/or added, and serves as an H chain variable region against human IL-18, (g) a polypeptide consisting of an amino acid sequence shown in SEQ ID NO: 4 or 6, and (h) a polypeptide which consists of an amino acid sequence in which one or several amino acids in the amino acid sequence shown in SEQ ID NO: 4 or 6 are substituted, deleted, inserted, and/or added, and serves as an L chain variable region against human IL-18.

[42] An H chain variable region fragment of a human-derived antibody against human IL-18, the H chain variable region fragment consisting of a polypeptide of the following (e) or (f):

(e) a polypeptide consisting of an amino acid sequence shown in SEQ ID NO: 3 or 5, and (f) a polypeptide which consists of an amino acid sequence in which one or several amino acids in the amino acid sequence shown in SEQ ID NO: 3 or 5 are substituted, deleted, inserted, and/or added, and serves as an H chain variable region against human IL-18.

[43] An L chain variable region fragment of a human-derived antibody against human IL-18, the L chain variable region fragment consisting of a polypeptide of the following (g) or (h):

(g) a polypeptide consisting of an amino acid sequence shown in SEQ ID NO: 4 or 6, and (h) a polypeptide which consists of an amino acid sequence in which one or several amino acids in the amino acid sequence shown in SEQ ID NO: 4 or 6 are substituted, deleted, inserted, and/or added, and serves as an L chain variable region against human IL-18.

[44] A single-chain variable fragment of a human-derived antibody against human IL-18, wherein the H chain variable region fragment comprising the complementarity determining regions of the H chain according to [40] or the H chain variable region fragment according to [42] is linked to the L chain variable region fragment comprising the complementarity determining regions of the L chain according to [40] or the L chain variable region fragment according to [43].

[45] A human-derived antibody against human IL-18, wherein a human-derived constant region is linked to the H chain variable region fragment comprising the complementarity determining regions of the H chain according to [40] or the H chain variable region fragment according to [42] and/or the L chain variable region fragment comprising the complementarity determining regions of the L chain according to [40] or the L chain variable region fragment according to [43], or a fragment thereof

[46] The fragment of the antibody according to [45], wherein the fragment of the antibody is Fab, Fab', F(ab')2, scAb, or scFvFc.

[47] A modified antibody, wherein a modifier is bound to the antibody or the fragment thereof according to any of [35] to [46].

[48] A gene encoding the antibody or the fragment thereof according to any of [35] to [47].

[49] The gene according to [48], wherein the gene has a nucleotide sequence shown in any of SEQ ID NOs: 3 to 6 as an open reading frame region.

[50] A recombinant expression vector comprising the gene according to [48] or [49].

[51] A transformant in which the gene according to [48] or [49] is introduced.

[52] A method for producing a human-derived human anti-human IL-18 antibody or a fragment thereof, comprising allowing a host to express the gene according to [48] or [49].

[53] A detection apparatus for human IL-18 comprising the antibody or the fragment thereof according to any of [35] to [46] or the modified antibody according to [47].

[54] A diagnostic kit for a disease which measures a human IL-18 level in a test sample, the diagnostic kit comprising a human IL-18 detection reagent consisting of the antibody or the fragment thereof according to any of [35] to [46] or the modified antibody according to [47].

[55] The diagnostic kit according to [54], wherein the disease is hyper-IL-18-naemia in a human.

[56] The diagnostic kit according to [54] or [55], wherein the disease is one or more diseases selected from the group consisting of allergy, inflammation, and chronic immune disorder.

[57] The diagnostic kit according to any of [54] to [56], wherein the disease is one or more diseases selected from the group consisting of interstitial pneumonia, adult-onset Still's disease, chronic obstructive pulmonary disease, metabolic bone disease, multiple sclerosis, diabetes mellitus, atopic dermatitis, airway inflammation, airway hyperresponsiveness (AHR), asthma, and serious organ damages in the liver, the kidney, and the intestine.

[58] A method for diagnosing a disease on the basis of a human IL-18 level in a test sample measured using the diagnostic kit according to any of [54] to [57].

[59] A human IL-18 activity inhibitor containing any of the following antagonists as an active ingredient:
  i) the antibody or the fragment thereof according to any of [35] to [46],
  ii) the modified antibody according to [47], and
  iii) a low-molecular compound molecularly designed on the basis of an antigenic determinant on human IL-18 that is recognized by the antibody, the fragment of the antibody, or the modified antibody according to any of i) or ii).

[60] A human IL-18 binding inhibitor containing the antagonist according to [59] as an active ingredient, wherein the human IL-18 binding inhibitor inhibits the binding between human IL-18 and human IL-18 receptor.

[61] An interferon-γ production inhibitor containing the antagonist according to [59] as an active ingredient.

[62] A gene therapeutic agent comprising the gene according to [48] or [49].

[63] A therapeutic agent for a disease, comprising the human IL-18 activity inhibitor according to [59], the human IL-18 binding inhibitor according to [60], the interferon-γ production inhibitor according to [61], or the gene therapeutic agent according to [62].

[64] The therapeutic agent for a disease according to [63], wherein the disease is hyper-IL-18-naemia in a human.

[65] The therapeutic agent for a disease according to [63] or [64], wherein the disease is one or more diseases selected from the group consisting of allergy, inflammation, and chronic immune disorder.

[66] The therapeutic agent for a disease according to any of [63] to [65], wherein the disease is one or more diseases selected from the group consisting of interstitial pneumonia, adult-onset Still's disease, chronic obstructive pulmonary disease, metabolic bone disease, multiple sclerosis, diabetes mellitus, atopic dermatitis, airway inflammation, airway hyperresponsiveness (AHR), asthma, and serious organ damages in the liver, the kidney, and the intestine, etc.

[67] The therapeutic agent for a disease according to any of [63] to [66], wherein the therapeutic agent inhibits the binding between human IL-18 and human IL-18 receptor.

[68] The therapeutic agent for a disease according to any of [63] to [67], wherein the therapeutic agent inhibits interferon-γ production from a helper T1 cell.

[69] A method for treating a disease, comprising administering the therapeutic agent for a disease according to any of [63] to [68].

[70] A method for preparing the antibody or the fragment thereof according to any of [35] to [69], comprising binding human IL-18 to a support in the form of beads via a linker and then reacting the support with a phage display library under conditions that expose and maintain an IL-18BP recognition region of the human IL-18.

Furthermore, the present invention can provide a human-derived antibody against human IL-18 and a fragment thereof, not a chimeric antibody or a humanized antibody as before, and methods for using the same. Hence, a therapeutic drug is expected which maintains remarkable therapeutic effects and high safety even if repeated administration and long-term administration is performed in the treatment of a disease in which human IL-18 is involved directly or indirectly.

Other objects, features, and advantages of the present invention will be fully understood by the description given below.

Effects of the Invention

The human anti-IL-18 antibody and the antibody fragment of the present invention have the following features and as such, are useful as safer and more efficient IL-18 antagonists:
  (1) having the same working mechanism as in IL-18BP, which is an organism-derived natural IL-18 antagonist;
  (2) being able to act synergistically with IL-18BP; and
  (3) being able to be administered at a lower concentration because $IC_{50}$ in the inhibition of IFN-γ production is low, as compared with previously reported antagonists (IL-18BP and antibodies).

EMBODIMENTS FOR CARRYING OUT THE INVENTION

Figure 1:
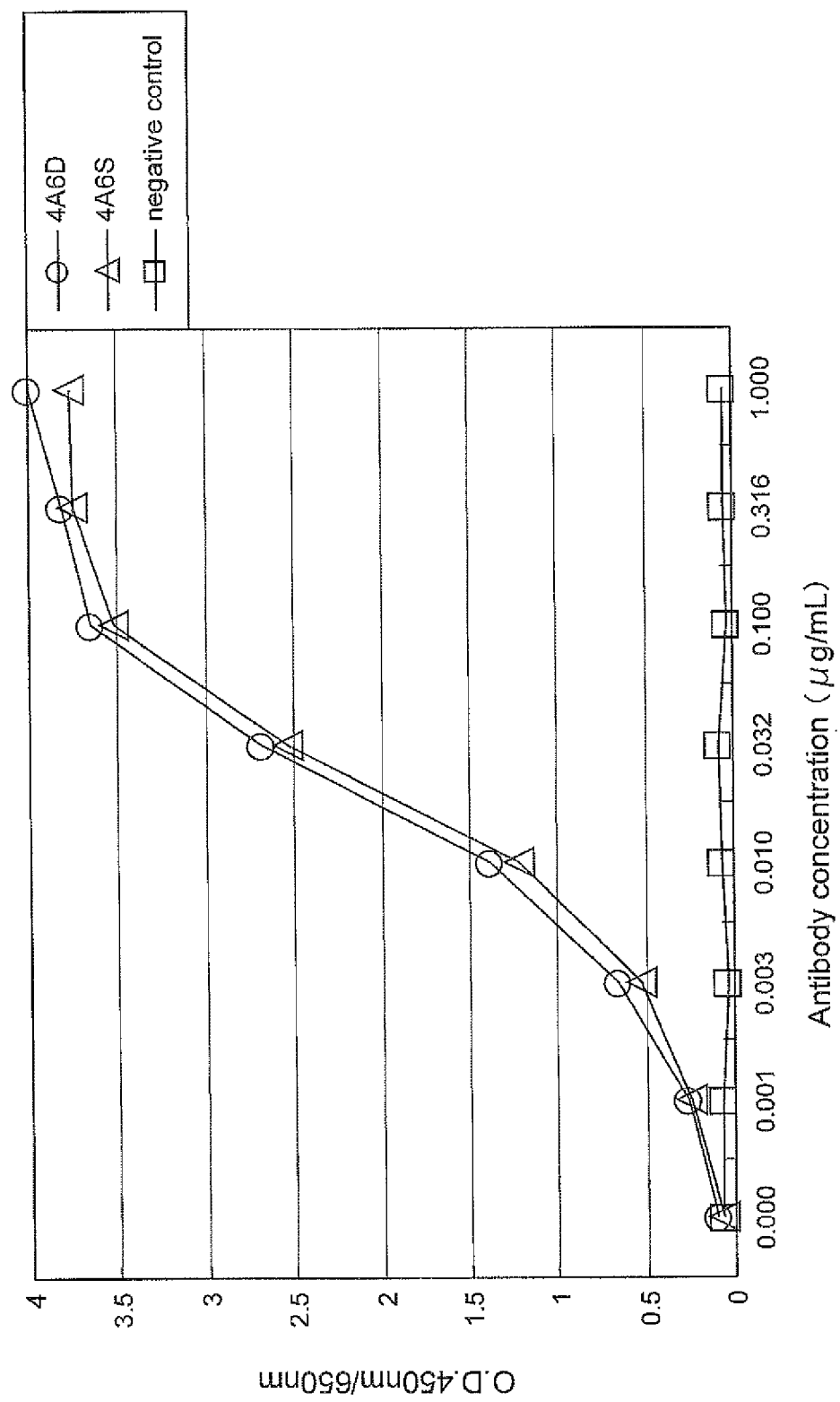
FIG. 1 is a graph showing results of a binding activity test on an anti-human IL-18 antibody.

Specific aspects of the present invention will be described below. However, the present invention is not intended to be limited by the description below.

(1) Antibody and Fragment Thereof

The present inventors have conducted studies on a human anti-human IL-18 antibody against human interleukin-18 (IL-18). As a result, it has been revealed that a human-derived single-chain variable fragment (scFv) obtained by a phage display method and an antibody derived from the fragment inhibit signal transduction and IFN-γ production induced by human IL-18. Further, the amino acid sequences of complementarity determining regions (CDRs) and H chain and L chain variable regions in this single-chain variable fragment (scFv) and the nucleotide sequences of genes encoding them have been identified (SEQ ID NOs: 1 and 2). As a result of analyzing an epitope for a human IL-18 antibody, it has also been revealed that the epitope is a region comprising lysine at the position 53 of human IL-18.

In one embodiment, the human anti-human IL-18 antibody is an antibody which reacts with human IL-18 and does not react with a K53A variant of human IL-18.

Here, the phrase "human anti-human IL-18 antibody reacts with human IL-18" means that the human anti-human IL-18 antibody binds to human IL-18. More specifically, it means that the ability of the human anti-human IL-18 antibody to bind to human IL-18 is significantly higher than the ability of a negative control antibody to bind to human IL-18. An antibody for which it is evident that human IL-18 is not an antigen can be used as the negative control antibody, and, for example, a human anti-HBs antibody can be used. The ability of the negative control antibody or the human anti-human IL-18 antibody to bind to human IL-18 can be measured by a usual method such as ELISA.

Also, the phrase "human anti-human IL-18 antibody does not react with a K53A variant of human IL-18" means that the ability of the human anti-human IL-18 antibody to bind to a K53A variant of human IL-18 is significantly lower than the ability of the human anti-human IL-18 antibody to bind to human IL-18. The ability of the human anti-human IL-18 antibody to bind to human IL-18 or the K53A variant of human IL-18 can be measured by a usual method such as ELISA.

Hereinafter, the meanings of the terms "react" and "not react" are the same as those mentioned above.

The human anti-human IL-18 antibody may be a recombinant. The recombinant means a molecule produced by a genetic engineering approach. The human anti-human IL-18 antibody may be freeze-dried. Alternatively, the human anti-human IL-18 antibody may be in the form of a composition mixed with a pharmaceutically acceptable carrier.

In one embodiment, the human anti-human IL-18 antibody is an antibody which reacts with human IL-18 and does not react with a complex of human IL-18 and human IL-18BP.

In one embodiment, the human anti-human IL-18 antibody is an antibody in which
complementarity determining region (CDR)1 of an H chain consists of the amino acid sequence of SEQ ID NO: 7 or an amino acid sequence in which one or several amino acids in the amino acid sequence of SEQ ID NO: 7 are deleted, substituted, or added,
CDR2 of the H chain consists of the amino acid sequence of SEQ ID NO: 8 or an amino acid sequence in which one or several amino acids in the amino acid sequence of SEQ ID NO: 8 are deleted, substituted, or added,
CDR3 of the H chain consists of the amino acid sequence of SEQ ID NO: 9 or an amino acid sequence in which one or several amino acids in the amino acid sequence of SEQ ID NO: 9 are deleted, substituted, or added,
CDR1 of an L chain consists of the amino acid sequence of SEQ ID NO: 10 or an amino acid sequence in which one or several amino acids in the amino acid sequence of SEQ ID NO: 10 are deleted, substituted, or added,
CDR2 of the L chain consists of the amino acid sequence of SEQ ID NO: 11 or an amino acid sequence in which one or several amino acids in the amino acid sequence of SEQ ID NO: 11 are deleted, substituted, or added, and
CDR3 of the L chain consists of the amino acid sequence of SEQ ID NO: 12 or an amino acid sequence in which one or several amino acids in the amino acid sequence of SEQ ID NO: 12 are deleted, substituted, or added, wherein
the antibody reacts with human IL-18 and does not react with a K53A variant of human IL-18, or the antibody reacts with human IL-18 and does not react with a complex of human IL-18 and human IL-18BP.

In one embodiment, the human anti-human IL-18 antibody is an antibody in which
an H chain variable region consists of an amino acid sequence of SEQ ID NO: 3 or 5 or an amino acid sequence in which one or several amino acids in the amino acid sequence of SEQ ID NO: 3 or 5 are deleted, substituted, or added, and
an L chain variable region consists of an amino acid sequence of SEQ ID NO: 4 or 6 or an amino acid sequence in which one or several amino acids in the amino acid sequence of SEQ ID NO: 4 or 6 are deleted, substituted, or added, wherein
the antibody reacts with human IL-18 and does not react with a K53A variant of human IL-18, or the antibody reacts with human IL-18 and does not react with a complex of human IL-18 and human IL-18BP.

In one embodiment, the H chain variable region fragment is an antibody fragment consisting of an amino acid sequence of SEQ ID NO: 3 or 5 or an amino acid sequence in which one or several amino acids in the amino acid sequence of SEQ ID NO: 3 or 5 are deleted, substituted, or added, wherein the antibody fragment reacts with human IL-18 and does not react with a K53A variant of human IL-18 or a complex of human IL-18 and human IL-18BP.

The H chain variable region fragment exhibits the reactivity mentioned above alone or in combination with an arbitrary L chain variable region fragment.

The combination of the H chain variable region fragment with an L chain variable region fragment includes the preparation of the H chain variable region fragment and the L chain variable region fragment into a structure such as a full-length antibody, a single-chain variable fragment (scFv), Fab, Fab', F(ab')₂, scAb, or scFvFc.

In one embodiment, the L chain variable region fragment is an antibody fragment consisting of an amino acid sequence of SEQ ID NO: 4 or 6 or an amino acid sequence in which one or several amino acids in the amino acid sequence of SEQ ID NO: 4 or 6 are deleted, substituted, or added, wherein the antibody fragment reacts with human IL-18 and does not react with a K53A variant of human IL-18 or a complex of human IL-18 and human IL-18BP.

The L chain variable region fragment exhibits the reactivity mentioned above alone or in combination with an arbitrary H chain variable region fragment.

In one embodiment, the single-chain variable fragment (scFv) of the human anti-human IL-18 antibody is one in which the following H chain variable region fragment and L chain variable region fragment are linked:

H chain variable region fragment:
an H chain variable region fragment consisting of
CDR1 consisting of the amino acid sequence of SEQ ID NO: 7 or an amino acid sequence in which one or several amino acids in the amino acid sequence of SEQ ID NO: 7 are deleted, substituted, or added, CDR2 consisting of the amino acid sequence of SEQ ID NO: 8 or an amino acid sequence in which one or several amino acids in the amino acid sequence of SEQ ID NO: 8 are deleted, substituted, or added, and CDR3 consisting of the amino acid sequence of SEQ ID NO: 9 or an amino acid sequence in which one or several amino acids in the amino acid sequence of SEQ ID NO: 9 are deleted, substituted, or added, or an H chain variable region fragment consisting of an amino acid sequence of SEQ ID NO: 3 or 5 or an amino acid sequence in which one or several amino acids in the amino acid sequence of SEQ ID NO: 3 or 5 are deleted, substituted, or added; and L chain variable region fragment:

an L chain variable region fragment consisting of

CDR1 consisting of the amino acid sequence of SEQ ID NO: 10 or an amino acid sequence in which one or several amino acids in the amino acid sequence of SEQ ID NO: 10 are deleted, substituted, or added, CDR2 consisting of the amino acid sequence of SEQ ID NO: 11 or an amino acid sequence in which one or several amino acids in the amino acid sequence of SEQ ID NO: 11 are deleted, substituted, or added, and CDR3 consisting of the amino acid sequence of SEQ ID NO: 12 or an amino acid sequence in which one or several amino acids in the amino acid sequence of SEQ ID NO: 12 are deleted, substituted, or added, or an L chain variable region fragment consisting of an amino acid sequence of SEQ ID NO: 4 or 6 or an amino acid sequence in which one or several amino acids in the amino acid sequence of SEQ ID NO: 4 or 6 are deleted, substituted, or added.

In one embodiment, the human anti-human IL-18 antibody is one in which a constant region of a human-derived antibody is linked to the following H chain variable region fragment and/or L chain variable region fragment:

H chain variable region fragment:

an H chain variable region fragment consisting of

CDR1 consisting of the amino acid sequence of SEQ ID NO: 7 or an amino acid sequence in which one or several amino acids in the amino acid sequence of SEQ ID NO: 7 are deleted, substituted, or added, CDR2 consisting of the amino acid sequence of SEQ ID NO: 8 or an amino acid sequence in which one or several amino acids in the amino acid sequence of SEQ ID NO: 8 are deleted, substituted, or added, and CDR3 consisting of the amino acid sequence of SEQ ID NO: 9 or an amino acid sequence in which one or several amino acids in the amino acid sequence of SEQ ID NO: 9 are deleted, substituted, or added, or an H chain variable region fragment consisting of an amino acid sequence of SEQ ID NO: 3 or 5 or an amino acid sequence in which one or several amino acids in the amino acid sequence of SEQ ID NO: 3 or 5 are deleted, substituted, or added; and L chain variable region fragment:

an L chain variable region fragment consisting of

CDR1 consisting of the amino acid sequence of SEQ ID NO: 10 or an amino acid sequence in which one or several amino acids in the amino acid sequence of SEQ ID NO: 10 are deleted, substituted, or added, CDR2 consisting of the amino acid sequence of SEQ ID NO: 11 or an amino acid sequence in which one or several amino acids in the amino acid sequence of SEQ ID NO: 11 are deleted, substituted, or added, and CDR3 consisting of the amino acid sequence of SEQ ID NO: 12 or an amino acid sequence in which one or several amino acids in the amino acid sequence of SEQ ID NO: 12 are deleted, substituted, or added, or an L chain variable region fragment consisting of an amino acid sequence of SEQ ID NO: 4 or 6 or an amino acid sequence in which one or several amino acids in the amino acid sequence of SEQ ID NO: 4 or 6 are deleted, substituted, or added.

The antibody according to the present embodiment or the fragment thereof includes antibodies and fragments thereof shown in the following (i) to (vii):

(i) A VH chain fragment (H chain variable region fragment) comprising polypeptides consisting of the amino acid sequences shown in SEQ ID NOs: 7 to 9, or polypeptides which consist of amino acid sequences in which one or several amino acids in the amino acid sequences shown in SEQ ID NOs: 7 to 9 are substituted, deleted, inserted, and/or added, and serve as complementarity determining regions of an H chain against human IL-18.

The phrase "serving as complementarity determining regions of an H chain against human IL-18" means exhibiting reactivity with human IL-18 alone or in combination with an arbitrary L chain variable region fragment.

The amino acid sequence of a VH chain is shown in SEQ ID NOs: 3 and 5. The amino acid sequences of complementarity determining regions (CDR1 to CDR3) in this VH chain are shown in SEQ ID NOs: 7 to 9. Specifically, the amino acid sequence of the positions 31 to 35 in the amino acid sequence of a VH chain shown in any of SEQ ID NOs: 3 and 5 corresponds to CDR1 (SEQ ID NO: 7), the amino acid sequence of the positions 50 to 66 therein corresponds to CDR2 (SEQ ID NO: 8), and the amino acid sequence of the positions 99 to 109 therein corresponds to CDR3 (SEQ ID NO: 9).

(ii) A VH chain fragment (H chain variable region fragment) consisting of a polypeptide consisting of an amino acid sequence shown in SEQ ID NO: 3 or 5, or a polypeptide which consists of an amino acid sequence in which one or several amino acids in the amino acid sequence shown in SEQ ID NO: 3 or 5 are substituted, deleted, inserted, and/or added, and serves as an H chain variable region against human IL-18.

(iii) A VL chain fragment (L chain variable region fragment) comprising polypeptides consisting of the amino acid sequences shown in SEQ ID NOs: 10 to 12, or polypeptides which consist of amino acid sequences in which one or several amino acids in the amino acid sequences shown in SEQ ID NOs: 10 to 12 are substituted, deleted, inserted, and/or added, and serve as complementarity determining regions of an L chain against human IL-18.

The phrase "serving as complementarity determining regions of an L chain against human IL-18" means exhibiting reactivity with human IL-18 alone or in combination with an arbitrary H chain variable region fragment.

SEQ ID NOs: 4 and 6 show the amino acid sequence of a VL chain. SEQ ID NOs: 10 to 12 show the amino acid sequences of complementarity determining regions (CDR1 to CDR3) in this VL chain. Specifically, the amino acid sequence of the positions 23 to 36 in the amino acid sequence of a VL chain shown in any of SEQ ID NOs: 4 and 6 5 corresponds to CDR1 (SEQ ID NO: 10), the amino acid sequence of the positions 52 to 58 therein corresponds to CDR2 (SEQ ID NO: 11), and the amino acid sequence of the positions 91 to 101 therein corresponds to CDR3 (SEQ ID NO: 12).

(iv) A VL chain fragment (L chain variable region fragment) consisting of a polypeptide consisting of an amino acid sequence shown in SEQ ID NO: 4 or 6, or a polypeptide which consists of an amino acid sequence in which one or several amino acids in the amino acid sequence shown in SEQ ID NO: 4 or 6 are substituted, deleted, inserted, and/or added, and serves as an L chain variable region against human IL-18.

(v) A single-chain variable fragment (scFv) prepared by linking the VH chain of above (i) or (ii) and the VL chain of above (iii) or (iv).

(vi) A human-derived antibody prepared by linking a human-derived constant region to the VH chain of above (i) or (ii) and/or the VL chain of above (iii) or (iv), or a fragment thereof.

(vii) A human anti-human IL-18 antibody whose epitope is a region comprising lysine at the position 53 of human IL-18.

In the case of linking the VH chain and the VL chain in above (v) and (vi), they are usually linked by an appropriate peptide linker or the like. For example, an arbitrary single-chain peptide consisting of 10 to 25 amino acid residues is used as this peptide linker. Specific examples of the peptide linker include $(GGGGS)_3$.

The antibody prepared by linking a human-derived constant region to the VH chain and/or the VL chain, or the fragment thereof, described in above (vi) may be a complete antibody (full-length antibody), Fab, Fab', $F(ab')_2$, or scAb or scFvFc having at least a partial Fc moiety. The scAb is one in which a partial domain (C domain) of a constant region of an L chain or an H chain is bound with scFv, and the scFvFc is one in which CH1 and CH2 of an H chain are bound with scFv.

Moreover, the aforementioned antibody is meant to also encompass a protein structurally related to the antibody, i.e., means an immunoglobulin. Furthermore, the antibody of the present embodiment may be any class of IgA, IgD, IgE, IgG, and IgM. In other words, it may be a monomer or may be a multimer such as a dimer, a trimer, a tetramer, or a pentamer.

Here, the phrase "one or several amino acids are substituted, deleted, inserted, and/or added" means that the number of amino acids to an extent that can be substituted, deleted, inserted, and/or added by a heretofore known variant protein preparation method such as site-directed mutagenesis are substituted, deleted, inserted, and/or added. Thus, for example, the polypeptides of the "amino acid sequences in which one or several amino acids in the amino acid sequences shown in SEQ ID NOs: 7 to 9 are substituted, deleted, inserted, and/or added" are variant peptides of the polypeptides of the "amino acid sequences shown in SEQ ID NOs: 7 to 9", and the "variation" described here mainly means a variation artificially introduced by a heretofore known variant protein preparation method.

For example, the "amino acid sequence in which one or several amino acids in the amino acid sequence of SEQ ID NO: 7 are deleted, substituted, or added" may be an amino acid sequence having 85% or higher, 90% or higher, or 95% or higher homology to the amino acid sequence of SEQ ID NO: 7. The same holds true for amino acid sequences other than SEQ ID NO: 7.

In the case of using the antibody of the present embodiment or the fragment thereof as a therapeutic drug (in the case of administering the antibody of the present embodiment or the fragment thereof to a human) as mentioned later, the "variation" is performed in a range in which a human-derived structure or a human does not cause immune response. In the case of using it as a detection apparatus, a diagnostic kit, or the like (in the case of not administering it to a human), there is no particular limitation. Also, in the case of administering the antibody of the present embodiment or the fragment thereof to a human, it is preferable to perform the variation in a range that maintains the higher order structures of CDRs recognizing the antigen.

Since CDRs are regions recognizing the antigen, human IL-18 is recognized by the complementarity determining regions (CDRs) of the antibody according to the present embodiment or the fragment thereof. Thus, an antibody or a fragment having at least the CDRs mentioned above can specifically recognize human IL-18. That is, the VH chain and the VL chain mentioned above may be amino acid sequences comprising at least CDRs of the VH chain and the VL chain, wherein the other regions are a human-derived VH chain and VL chain. By this, the specificity for human IL-18 is retained. However, CDRs are specifically constructed by the primary structures and higher order structures of variable regions of an H chain and an L chain. Therefore, in the case of constituting a human anti-IL-18 antibody comprising at least CDRs of the VH chain and the VL chain, wherein the other regions are a human-derived VH chain and VL chain, it is preferable to prepare it as an antibody having the specificity for human IL-18. For example, it is preferable to prepare the antibody having the specificity for human IL-18 by maintaining the higher order structures of at least CDRs.

As shown in Examples mentioned later, as a result of conducting detailed analysis on the scFv mentioned above, the following findings were gained as to effects and properties thereof:

specifically binding to human IL-18 and monkey IL-18, and inhibiting signal transduction and IFN-γ production induced by human IL-18 and monkey IL-18.

Moreover, the antibody of the present embodiment or the fragment thereof may comprise an additional polypeptide. Examples of the case where such a polypeptide is added include the case where the antibody of the present embodiment or the fragment thereof is epitope-tagged with His, Myc, Flag, or the like. Specifically, examples of the additional polypeptide include His, Myc, and FLAG.

Furthermore, the antibody of the present embodiment and the fragment thereof may be bound with a modifier in order to improve stability and antibody titer. Specifically, the antibody of the present embodiment and the fragment thereof may be a modified antibody. Examples of this modifier include sugar chains and polymers. In the case of performing modification with a sugar chain, there is the possibility that the sugar chain has certain biological activity. In the case of performing modification with a simple polymer such as polyethylene glycol (PEG), the polymer itself does not exhibit biological activity. There is further the possibility that, by the PEGylation, absorption in the liver is suppressed or stability in blood is improved. In short, a simple polymer such as PEG is preferable as the modifier.

In the case of use as a therapeutic drug, the modification of the antibody of the present embodiment and the fragment thereof with the modifier is performed in a range in which a human does not cause immune response, as in the preparation of the variant peptide mentioned above. In the case of use as a detection apparatus, a diagnostic kit, or the like, there is no particular limitation. Also, in the case of administering the antibody of the present embodiment or the fragment thereof to a human, it is preferable to perform the modification in a range that maintains the higher order structures of CDRs recognizing the antigen.

Since the antibody of the present embodiment and the fragment thereof have a human-derived amino acid sequence, the possibility that an anti-antibody that inhibits the activity of the antibody is formed is very low. In addition, the antibody of the present embodiment and the fragment thereof have the effect of binding strongly to human IL-18, thereby inhibiting the biological activity such as IFN-γ production, and are therefore expected to inhibit various immune responses evoked by human IL-18. Accordingly, the antibody of the present embodiment and the fragment thereof may be used for the treatment of a disease mentioned later in which human IL-18 is involved directly or indirectly.

(2) Gene

A gene encoding the antibody or the fragment thereof described in above "(1) Antibody and fragment thereof" is included in an embodiment of the present invention. Genes consisting of the nucleotide sequences shown in SEQ ID NOs: 1 and 2, genes consisting of nucleotide sequences having 85% or higher, 90% or higher, or 95% or higher homology to the nucleotide sequences shown in SEQ ID NOs: 1 and 2, genes encoding the amino acid sequences shown in SEQ ID NOs: 3 to 6, genes having these genes as open reading frame (ORF) regions, and altered genes in which a portion of the nucleotide sequences of these genes has been altered, etc., are included in the present embodiment.

The gene mentioned above is a recombinant gene obtained from a phage display library and is not naturally present. Also, the gene may be cDNA.

The gene encodes the antibody of the preceding embodiment or the fragment thereof and can therefore be introduced into an appropriate host (e.g., a bacterium or a yeast) to express the antibody of the preceding embodiment or the fragment thereof.

Furthermore, the "gene" may comprise sequences such as a sequence of an untranslated region (UTR) and a vector sequence (including an expression vector sequence), in addition to the sequence encoding the antibody or the fragment thereof described in above "(1) Antibody and fragment thereof". For example, genes consisting of the nucleotide sequences shown in SEQ ID NOs: 1 and 2 or genes encoding the amino acid sequences shown in SEQ ID NOs: 3 to 6 are ligated with vector sequences, which can then be amplified in an appropriate host, thereby amplifying the gene of the present embodiment as desired. Also, a partial sequence of the gene of the present embodiment may be used as a probe. Moreover, as mentioned later, the gene of the present embodiment may be used as a gene therapeutic agent for a disease in which human IL-18 is involved.

(3) Methods for Obtaining and Producing Antibody and Fragment Thereof

The antibody and the fragment thereof described in above "(1) Antibody and fragment thereof" can be obtained, as shown in Examples mentioned later, for example, by using a so-called phage display method (e.g., MRC, UC, CAT, MEDIMMUNE, XOMA, DYAX, or MORPHOSYS) and a screening method in a state where an IL-18BP recognition region present on the IL-18 molecule is exposed and maintained.

Therefore, the present invention includes a method for preparing the antibody or the fragment thereof described in above "(1) Antibody and fragment thereof", comprising binding IL-18 to a support in the form of beads via a linker and then reacting the support with a phage display library under conditions that expose and maintain an IL-18BP recognition region of the IL-18.

Alternatively, the antibody and the fragment thereof described in above "(1) Antibody and fragment thereof" can be produced by allowing a host to express the gene described in above "(2) Gene". The methods for obtaining and producing the antibody and the fragment thereof are not limited thereto.

More specifically, mRNAs are extracted from the peripheral blood B lymphocytes of a healthy person and amplified by RT-PCR using primer pairs defining both ends of VH chains and VL chains of immunoglobulin genes to obtain V region populations of H chains and L chains having diverse sequences. Next, a DNA encoding a peptide linker moiety is further amplified in combination with a primer pair defining it such that both ends thereof are linked to an H chain and an L chain, respectively, to prepare diverse scFv DNA populations by random combinations of the V regions of H chains and L chains. The obtained scFv DNAs are incorporated into phagemid vectors to prepare an scFv display phage library. The quality and diversity of this library are very important factors for obtaining an effective antibody.

Although human IL-18, which is a target protein, is usually immobilized as the first choice onto a plastic plate, the human IL-18 is biotinylated using a biotinylating reagent comprising a linker of a proper length in order to expose and maintain an IL-18BP recognition region present on the IL-18 molecule. The length of the linker is, for example, 3 to 100 angstrom, for example, 5 to 50 angstrom, or, for example, 10 to 30 angstrom.

Next, this library is reacted in a liquid phase with biotinylated human IL-18 bound with streptavidin magnetic beads, and unreacted scFv display phages are removed by washing, followed by the elution of an scFv phage clone bound with human IL-18 using an acid. scFv DNA is prepared from the separated phage clone, and this is incorporated into an expression vector. A host transformed with the expression vector is cultured according to a conventional method to obtain only the scFv protein of interest.

SEQ ID NOs: 1 and 2 are the nucleotide sequences of cDNAs encoding the single-chain variable regions (scFvs) against human IL-18 obtained by the phage display antibody method. Also, SEQ ID NOs: 3 and 5 are the amino acid sequences of VH chains of the obtained anti-human IL-18 antibodies, and SEQ ID NOs: 4 and 6 are the amino acid sequences of VL chains of the obtained anti-human IL-18 antibodies.

The gene encoding scFv can be expressed in, for example, *Escherichia coli*. In the case of *Escherichia coli*, it can be expressed by functionally linking a useful promoter conventionally used, a signal sequence for antibody secretion, and the like to the gene encoding scFv to be expressed. Examples of the promoter include lacZ promoter and araB promoter. In the case of expression in the periplasm of *Escherichia coli*, it is preferable to use pelB signal sequence (Non Patent Literature 25) as the signal sequence for secretion of scFv. The signal sequence of g3 protein of M13 phage can also be used for secretion into a culture supernatant.

The scFv expressed as described above can be separated from the inside or outside of the host cells and homogeneously purified. The scFv expressed in the present embodiment can be easily purified in a short time by affinity chromatography using a nickel column, because a His tag sequence is added to its C terminus. In addition, it is also possible to purify the scFv by combining usual separation and purification methods used for proteins. The antibody can be separated and purified by combining, for example, ultrafiltration, salting out, and column chromatography such as gel filtration/ion exchange/hydrophobic chromatography. It has been revealed that the scFv protein (polypeptide) thus obtained has binding activity against human IL-18 as shown in Examples mentioned later.

A method such as ELISA or BIACORE is used as a method for measuring the antigen binding activity of the antibody according to the present embodiment or the fragment thereof against human IL-18. In the case of using, for example, ELISA, a sample containing the anti-IL-18 antibody or the antibody fragment of interest, for example, a culture supernatant of *Escherichia coli* or a purified antibody, is added to a human IL-18-immobilized 96-well plate. Next, a secondary antibody labeled with an enzyme such as alkaline phosphatase is added thereto, and the plate is incubated and washed. Then, a chromogenic substrate paranitrophenyl phosphate is added thereto, and the absorbance can be measured, thereby evaluating the antigen binding activity.

(4) Recombinant Expression Vector and Transformant

A recombinant expression vector comprising the gene described in above "(2) Gene", i.e., the gene encoding the antibody or the fragment thereof described in above "(1) Antibody and fragment thereof", is included in an embodiment of the present invention. Examples thereof include recombinant expression vectors in which cDNAs of genes consisting of the nucleotide sequences shown in SEQ ID NOs: 1 and 2 or genes encoding the amino acid sequences shown in SEQ ID NOs: 3 to 6 are inserted. A plasmid, a phage, or a cosmid, or the like can be used in the preparation of the recombinant expression vector, though not particularly limited thereto.

As mentioned above, the recombinant expression vector comprises the gene of the preceding embodiment. The specific type of the vector is not particularly limited, and a vector that permits expression in host cells can be appropriately selected. Specifically, a promoter sequence is appropriately selected according to the type of the host cells in order to securely express the gene, and one in which this and the gene according to the preceding embodiment are incorporated in various plasmids can be used as an expression vector.

Various markers may be used in order to confirm whether or not the gene of the preceding embodiment is introduced in host cells and further whether or not the gene of the preceding embodiment is securely expressed in host cells. For example, a gene deleted in host cells is used as a marker, and a plasmid or the like comprising this marker and the gene of the preceding embodiment is introduced as an expression vector into host cells. By this, the introduction of the gene of the preceding embodiment can be confirmed from the expression of the marker gene. Alternatively, the antibody according to the preceding embodiment or the fragment thereof may be expressed as a fusion protein, and the antibody according to the preceding embodiment or the fragment thereof may be expressed, for example, as a GFP fusion protein by using *Aequorea victoria*-derived green fluorescent protein GFP as a marker.

The host cells are not particularly limited, and various conventionally known cells can be preferably used. Specifically, examples of the host cells in the case of the gene encoding the full-length antibody, described in above "(2) Gene" include animal cells including human- or mouse-derived cells as well as oocytes of *Caenorhabditis elegans* and *Xenopas laevis*, cultured cells of various mammals (rats, rabbits, pigs, monkeys, etc.), and cultured cells of insects such as *Drosophila melanogaster* and *Bombyx mori*, and examples of the host cells in the case of the gene encoding the antibody fragment include bacteria such as *Escherichia coli* and yeasts (*Saccharomyces cerevisiae* and *Schizosaccharomyces pombe*), though not particularly limited thereto.

The method for introducing the expression vector into the host cells, i.e., the transformation method, is not particularly limited, and a conventionally known method such as an electroporation method, a calcium phosphate method, a liposome method, or a DEAE dextran method can be preferably used.

The transformant of the present embodiment is a transformant in which the gene described in above "(2) Gene", i.e., the gene encoding the antibody or the fragment thereof described in above "(1) Antibody and fragment thereof", is introduced. Here, the phrase "gene is introduced" means that the gene is expressibly introduced in intended cells (host cells) by a heretofore known genetic engineering approach (gene manipulation technique). Also, the "transformant" is meant to include not only cells, tissues, and organs but also animal individuals. Examples of the intended animals include, but are not particularly limited to, mammals such as cattle, pigs, sheep, goats, rabbits, dogs, cats, guinea pigs, hamsters, mice, and rats. Particularly, rodents such as mice or rats are widely used as laboratory animals or disease model animals. Among them, mice can be used as laboratory animals or disease model animals, because a large number of inbred lines have been produced and techniques for culture of fertilized eggs, external fertilization, etc. have been organized. Knockout mice or the like are useful in the further functional analysis of the antibody or the fragment thereof, the development of a method for diagnosing a disease in which human IL-18 is involved, the development of a method for treating it, etc.

It is also possible to produce the antibody or the fragment thereof described in above "(1) Antibody and fragment thereof" with the transformant of the present embodiment prepared by using the recombinant expression vector of the present embodiment.

(5) Methods for Using Antibody and Fragment Thereof (5-1) Detection Apparatus for Human IL-18, Carrier for Purification, Detection Reagent, Diagnostic Kit for Disease, and Diagnosis Method The antibody or the fragment thereof, or the modified antibody described in above "(1) Antibody and fragment thereof" binds specifically and strongly to human IL-18 and as such, may be used in a detection apparatus for human IL-18, a carrier for purification, a detection reagent, a diagnostic kit for a disease, or the like mentioned later.

The detection apparatus of the present embodiment can be used for the purpose of, for example, detecting human IL-18 contained in a sample such as blood or urine. It can be further used for diagnosis or treatment in order to diagnose a disease in which human IL-18 is involved or in order to evaluate therapeutic effects. The detection apparatus for human IL-18 of the present embodiment comprises at least polypeptides consisting of the amino acid sequences of CDRs of the antibody described in "(1) Antibody and fragment thereof". The detection apparatus for human IL-18 can be used in the detection, measurement, or the like of IL-18 under various conditions. Examples of the human IL-18 detection apparatus include antibody chips and antibody columns in which the antibody or the fragment thereof described in above "(1) Antibody and fragment thereof", which specifically binds to human IL-18, is immobilized on substrates (carriers).

Moreover, the carrier for purification of human IL-18 according to the present embodiment comprises the antibody or the fragment thereof, or the modified antibody described in above "(1) Antibody and fragment thereof". The carrier for purification can be prepared by binding the antibody, etc., by a general method to a carrier usually used in chromatography. The carrier for purification can be used in the purification of human IL-18 by immunoaffinity chromatography. This purification method comprises the steps of: contacting the antibody of the preceding embodiment or the fragment thereof with a mixture of human IL-18 and other substances to adsorb the human IL-18 onto the antibody or the fragment thereof; and desorbing and collecting the adsorbed human IL-18 from the antibody or the fragment thereof.

The reagent of the present embodiment for detecting human IL-18 (human IL-18 detection reagent) consists of the antibody or the fragment thereof, or the modified antibody described in above "(1) Antibody and fragment thereof". According to the human IL-18 detection reagent, human IL-18 in a test sample can be analyzed rapidly and accurately in a qualitative or quantitative manner by label immunoassay such as radioimmunoassay, enzyme immunoassay, or fluorescent immunoassay. In this label immunoassay, the antibody or the fragment thereof is labeled with, for example, a radioactive substance, an enzyme, and/or a fluorescent material and used. Since the antibody and the fragment thereof specifically react with human IL-18 to cause immune response, the immune response can be measured with the labeling material as an index, thereby precisely detecting a very trace amount of human IL-18 in the test sample. The label immunoassay, compared with bioassay, has the features that: it can analyze a large number of test samples at once; the time and labor required for the analysis are merely small; and the analysis is highly precise.

The diagnostic kit for a disease of the present embodiment comprises the human IL-18 detection reagent. The diagnostic kit can be used for measuring a human IL-18 level in a test sample and diagnosing a disease associated with change in the expression level of IL-18. The diagnostic kit may comprise a human IL-18 standard serving as a human IL-18 concentration index, in addition to the detection reagent.

The diagnosis method of the present embodiment comprises measuring a human IL-18 level in a test sample (blood, a body fluid, a tissue, etc.) using the diagnostic kit and diagnosing a disease on the basis of the measurement results. The "disease" is a disease associated with change in the expression level of IL-18, and hyper-IL-18-naemia in a human mentioned later is included. Moreover, examples of the "disease" include allergy, inflammation, and chronic immune disorder and more specifically include interstitial pneumonia, adult-onset Still's disease, chronic obstructive pulmonary disease, metabolic bone disease, multiple sclerosis, diabetes mellitus, atopic dermatitis, airway inflammation, airway hyperresponsiveness (AHR), asthma, and serious organ damages in the liver, the kidney, and the intestine.

The detection method with the detection apparatus for human IL-18 of the present embodiment is useful in process control in producing human IL-18 and the quality control of products. Also, the diagnostic kit and the diagnosis method for a disease of the present embodiment are very useful for performing the diagnosis of various sensitive diseases, the evaluation of treatment of various diseases, the pathological control of diseases, etc., by using the levels of human IL-18 in tissues and body fluids as an index.

In general, an antibody used for diagnosis is prepared by immunizing a non-human animal such as a mouse, a rabbit, or a goat. However, in the immune system of an animal, lymphocytes producing antibodies binding to molecules constituting the body of the self are eliminated or deactivated. In short, an antibody for which a portion very similar between human IL-18 and animal IL-18 is an antigenic determinant is not included in an anti-human IL-18 antibody prepared by immunizing the animal.

In contrast to this, the antibody of the preceding embodiment is an antibody screened for from a phage library comprising a phage displaying a human anti-human IL-18 antibody. The mechanism that eliminates or deactivates antibodies, as in the animal, is not present in this phage. Hence, an anti-IL-18 antibody exhibiting binding specificity for an antigenic determinant common in IL-18 of humans and other animals, which cannot be prepared in animal immunity, is included in the antibody of the preceding embodiment. Provided that such an antibody is used in the detection apparatus and the diagnostic kit of the present embodiment, an IL-18-associated disease can be diagnosed not only in humans but also various animal disease models including monkeys.

(5-2) Human IL-18 Activity Inhibitor, Binding Inhibitor, IFN-γ Production Inhibitor, and Gene Therapeutic Agent The antibody or the fragment thereof described in "(1) Antibody and fragment thereof" binds to human IL-18 while inhibiting the binding to human IL-18 receptor, also inhibiting signal transduction mediated by this receptor, and further inhibiting IFN-γ production induced by human IL-18. Thus, the antibody, in other words, is a human IL-18 antagonist. Furthermore, this human IL-18 antagonist can be used as a human IL-18 activity inhibitor.

Specifically, human IL-18 activity inhibitors containing antagonists of the following (I) to (IV) as active ingredients are included in an embodiment of the present invention:

(I) the antibody described in above "(1) Antibody and fragment thereof", (II) the fragment of the antibody described in above "(1) Antibody and fragment thereof", (III) a modified antibody of the antibody or the fragment thereof described in above "(1) Antibody and fragment thereof", and (IV) a low-molecular compound molecularly designed on the basis of an antigenic determinant on human IL-18 recognized by the antibody, the fragment of the antibody, or the modified antibody described in above (I) to (III).

Here, the "human IL-18 activity inhibitor" inhibits the activity of human IL-18 and may be one antagonistically inhibiting the binding to human IL-18 receptor or one inhibiting human IL-18 signal transduction by binding to the complex with IL-18 receptor.

Human IL-18 binding inhibitors containing the antagonists of above (I) to (IV) as active ingredients, wherein the inhibitors inhibit the binding between human IL-18 and human IL-18 receptor are also included in the present embodiment. The "human IL-18 binding inhibitor" may be one antagonistically inhibiting the binding to human IL-18 receptor.

IFN-γ production inhibitors containing the antagonists of above (I) to (IV) as active ingredients are further included in the present embodiment. The "IFN-γ production inhibitor" may be one inhibiting IFN-γ production.

Moreover, the gene described in above "(2) Gene" may be used as a gene therapeutic agent for a disease in which human IL-18 is involved. Therefore, gene therapeutic agents comprising the gene described in above "(2) Gene" are included in an embodiment of the present invention. This gene therapeutic agent may be designed such that the antibody of the preceding embodiment or the fragment thereof is expressed in vivo after ingestion, thereby forming the antibody of the preceding embodiment or the fragment thereof in vivo after the ingestion of the therapeutic agent and imparting thereto effects similar to those of the inhibitors mentioned above.

(5-3) Therapeutic Agent for Disease

The antibody or the fragment thereof described in above "(1) Antibody and fragment thereof" has variable regions of a human-derived anti-human IL-18 antibody and strongly reacts with human IL-18 to exhibit an inhibitory effect on the binding between IL-18 and IL-18 receptor. It further inhibits various immune responses (inhibits IFN-γ production) evoked by IL-18. Therefore, the human IL-18 activity inhibitor, the human IL-18 binding inhibitor, the IFN-γ production inhibitor, or the gene therapeutic agent may be used as a therapeutic agent for a disease in which human IL-18 is involved (IL-18-associated disease).

The antibody described in above "(1) Antibody and fragment thereof" is a human-derived human anti-human IL-18 recognizing human IL-18. Specifically, the amino acid sequence of this antibody, unlike conventional chimeric antibodies and humanized antibodies, is wholly derived from a human. Thus, there is no risk of formation of an antibody (anti-antibody) blocking the effects of the antibody of the preceding embodiment. Hence, this antibody can sustain effects while maintaining high safety, even if repeated administration or long-term administration is performed.

A therapeutic agent for a disease (hereinafter, also referred to as a "disease therapeutic agent") comprising the human IL-18 activity inhibitor, the human IL-18 binding inhibitor, the IFN-γ production inhibitor, or the gene therapeutic agent is included in an embodiment of the present invention. Hyper-IL-18-naemia in a human is included as the disease. The hyper-IL-18-naemia in a human is various diseases caused chiefly by an active form of human IL-18 excessively produced by some stimulation derived from the inside or outside of cells. Moreover, examples of the disease include allergy, inflammation, and chronic immune disorder and more specifically include interstitial pneumonia, adult-onset Still's disease, chronic obstructive pulmonary disease, metabolic bone disease, multiple sclerosis, diabetes mellitus, atopic dermatitis, airway inflammation, airway hyperresponsiveness (AHR), asthma, and serious organ damages in the liver, the kidney, and the intestine.

Since it is only necessary that the disease therapeutic agent of the present embodiment exert its effects in vivo, for example, a polypeptide encoded by the nucleotide sequence shown in SEQ ID NO: 1 (or a human IL-18 activity inhibitor comprising this) may be administered or a prodrug form may be metabolized in vivo so that the polypeptide is expressed. Specifically, the disease therapeutic agent of the present embodiment may be one in which the human IL-18 antagonist (human IL-18 activity inhibitor) of any of above (I) to (IV) or the gene therapeutic agent is in a prodrug form. Specifically, it may be modified so as to become an active metabolite in vivo.

Alternatively, the disease therapeutic agent of the present embodiment may be a composition comprising pharmaceutically acceptable additives such as one or more types of excipients, one or more types of binders, one or more types of disintegrants, one or more types of lubricants, and one or more types of buffers.

Since the antibody of the preceding embodiment inhibits signal transduction and IFN-γ production induced by IL-18 stimulation as mentioned above, an antigenic determinant on IL-18 that exhibits the binding specificity between the antibody having such characteristics and human IL-18 can be elucidated, thereby enabling application to the development of a disease therapeutic agent which is a low-molecular compound. This antigenic determinant is called epitope. This epitope may be a primary amino acid sequence itself and may be a conformation constructed in a folded manner of a peptide chain. In either case, for example, a similar compound (mimic molecule) of the epitope can be designed by a "molecular template design method using monoclonal antibodies" proposed by Fukumoto et al. (Non Patent Literature 26). Here, the "low-molecular compound" refers to, for example, a compound having a molecular weight smaller than 10000, for example, a molecular weight smaller than 3000, generally used as a small molecule drug, not a compound having a relatively large molecular weight (molecular weight: 10000 or larger) such as a peptide or an antibody. A smaller molecular weight of the low-molecular compound is more preferable.

In the case of developing a peptide or a lower-molecular-weight compound as the low-molecular compound, it can be designed by a so-called in silico process of performing molecular design by focusing on the molecular structure of this mimic molecule. By thus performing the molecular design in silico, a low-molecular compound that may serve as a therapeutic drug can be selected as a lead compound inexpensively and rapidly.

Specifically, for example, in Examples mentioned later, CDRs of a human anti-human IL-18 scFv antibody are shown in SEQ ID NOs: 7 to 9 and 10 to 12. In general, CDRs in an antibody are regions (sites) recognizing the antigen. Specifically, CDRs serve as active centers of the antibody. In short, the scFv shown in Examples specifically recognizes human IL-18 through CDRs.

Thus, provided that a low-molecular compound is designed so as to be substantially identical (preferably, completely identical) to the higher order structures of these CDRs, the low-molecular compound can be used as a small molecule drug. In other words, the low-molecular compound is designed to be closer to the conformations of the CDRs. Although the method of the in silico process is not particularly limited, the design can be made on a computer on the basis of functional groups carried by CDRs and the higher order structures of CDRs by, for example, SBDD (structure based drug design) or CADD (computer-aided drug design).

The low-molecular compound thus designed has high stability, as compared with proteins (peptides) such as antibodies. Therefore, this low-molecular compound can be used as an easy-to-handle drug.

(5-4) Example of Application of Disease Therapeutic Agent—1

As mentioned above, the human IL-18 activity inhibitor, the human IL-18 binding inhibitor, the IFN-γ production inhibitor, or the gene therapeutic agent of the preceding embodiment may be used as a therapeutic agent for a disease in which human IL-18 is involved. Hereinafter, examples of the application of the disease therapeutic agent will be shown.

Interstitial pneumonia is a generic name for 200 or more diseases with the inflammation of the interstitium of the lung (including the pulmonary alveolar septum in the narrow sense and the interlobular septum, the neighborhood of the chest lining, etc., in the broad sense), among diseases in which bilateral diffuse shadows are observed on chest X-ray images. Of them, many interstitial pneumonia cases of unknown causes are present. In order to elucidate the role of IL-18 in vivo, the group of the Kurume University has administered IL-2 to mice and observed change derived from the administration of IL-18 in an activated state of lymphocytes (Non Patent Literature 27). As a result, it has been found that interstitial pneumonia is evoked by the administration of IL-18, and found that IL-18 is deeply involved in the pathogenesis of interstitial pneumonia. The group has further considered that the onset of interstitial pneumonia is prevented by suppressing the onset of excessive action of IL-18, and conducted studies by using IL-18 receptor (IL-18Rα) knockout mice in order to verify this hypothesis. As a result, it has been confirmed that the onset of interstitial pneumonia is prevented by suppressing the action of IL-18.

Meanwhile, in Example 6 mentioned later, it has been confirmed using human cells KG-1 that the anti-IL-18 antibody obtained by the present inventors has the ability to suppress the onset of action of IL-18.

As mentioned above, IL-18 stimulates lymphocytes in collaboration with IL-2, thereby causing serious interstitial pneumonia. Thus, for example, the disease therapeutic agent mentioned above may be used in the treatment of interstitial pneumonia.

(5-5) Example of Application of Disease Therapeutic Agent—2

Adult-onset Still's disease is a systemic inflammatory disease that manifests high fever, polyarticular pain, and eruption as chief signs. Although much still remains unknown about a cause of the disease, it has been reported from Canada that HLAB17, B18, B35, and DR2 are linked as genetic factors. Recently, the possibility has been pointed out that the polymorphisms of genes of cytokines such as IL-18 become risks for the onset. Cases having the onset after infection by a virus such as human parvovirus, rubella virus, EB virus, echovirus, cytomegalovirus, influenza, parainfluenza, coxsackievirus, herpes virus, hepatitis B virus, or hepatitis C virus or a bacterium such as *Mycoplasma, Chlamydia, Yersinia*, or *Brucella* have previously been reported as environmental factors. Thus, the theory of induction by infection in which the infection by a virus or a bacterium seems to be a factor inducing Still's disease has also been proposed. It is also known that cytokines play an important role in the onset and the pathogenesis. In Still's disease patients, IL-1, IL-6, IL-8, IFN-γ, TNF-α, M-CSF, and IL-18 are overexpressed. Among them, remarkably increased IL-18 has been found, suggesting that IL-18 is a cause of Still's disease. Thus, it is expected that the onset of Still's disease is prevented by suppressing the onset of action of IL-18.

In Example 6 mentioned later, it has been confirmed using human cells KG-1 that the anti-IL-18 antibody obtained by the present inventors has the ability to suppress the onset of action of IL-18. Thus, for example, the disease therapeutic agent mentioned above may be used for adult-onset Still's disease or the like.

(5-6) Example of Application of Disease Therapeutic Agent—3

IL-18 is produced not only from cells of the immune system such as dendritic cells and macrophages but also from various cells of none-immune systems including dermal keratinocytes, intestinal epithelial cells, and respiratory epithelial cells.

Also, IL-18 induces the production of IFN-γ from various cells of the immune system or non-immune systems in the presence of IL-12. On the other hand, IL-18 induces the production of Th2 cytokines (cytokines produced from helper T2 cells) such as IL-4 and IL-13 from NKT cells, T cells, and NK cells in the absence of IL-12 to induce IgE production in an antigen-nonspecific manner.

Moreover, IL-18 not only potentiates the production of IFN-γ belonging to Th1 cytokines by stimulating antigen-stimulated Th1 cells but also induces the production of IL-9 and IL-13 belonging to Th2 cytokines and further IL-8, which is a typical chemokine.

Furthermore, IL-18 can be transnasally administered together with OVA (IL-18 and OVA are administered) to mice to which OVA-specific Th1-type memory T cells are transferred, thereby inducing Th1-type bronchial asthma characterized by strong infiltrates of neutrophils, lymphocytes, macrophages, and eosinophils into the alveolus and the interstitium and airway hyperresponsiveness.

Furthermore, IL-18 directly stimulates mast cells and basophils in an antigen/IgE-independent manner. As a result, it induces the production of various cytokines and chemical transmitters to induce a natural type of atopy (IL-18-dependent inflammation).

As shown in Examples mentioned later, the anti-IL-18 antibody obtained by the present inventors inhibited the activity of IL-18 in various in vitro systems. Particularly, this antibody has the function of inhibiting the production of IFN-γ, which is a Th1 cytokine.

As described above, IL-18 is an important for allergic inflammations such as bronchial asthma and a natural type of atopic dermatitis, and the human IL-18 antagonists (of above (I) to (IV)) mentioned above may be used as therapeutic drugs therefor.

The antibody according to the preceding embodiment and the fragment thereof are a human anti-human IL-18 antibody and a fragment thereof which inhibit the binding to human IL-18 receptor. Thus, they may be used as therapeutic drugs (treatment methods) or preventive agents (prevention methods) for various inflammatory diseases caused by human IL-18.

The present invention also provides, for example, an important approach for developing a small molecule drug (chemically synthetic drug) inhibiting IL-18 activity by designing a low-molecular compound on the basis of the higher order structures of CDRs of an scFv antibody.

As mentioned above, the human anti-human IL-18 antibody of the preceding embodiment inhibits the binding to IL-18 receptor. Thus, this antibody is effective for the treatment and prevention of various diseases caused by IL-18, in addition to those described above.

The present inventors have succeeded in isolating scFv specifically binding to IL-18 from a phage display library displaying human single-chain variable fragments (scFvs). This single-chain variable fragment can also specifically inhibit the binding to IL-18 receptor.

EXAMPLES

Hereinafter, the present invention will be described in detail with reference to Examples. The present invention is not intended to be limited by the description of Examples below, and various changes and modifications can be made within the scope of the present invention.

Example 1

Biotinylation of Cytokine

Cytokines human IL-18 (MBL Medical & Biological Laboratories, Co., Ltd.), monkey IL-18 (Thermo Fisher Scientific K.K.), rat IL-18 (*Acris* Antibodies GmbH), mouse IL-18 (MBL Medical & Biological Laboratories, Co., Ltd.), human IL-1β (Funakoshi Corp.), and human IL-33 (MBL Medical & Biological Laboratories, Co., Ltd.) were biotinylated using Biotin-PEAC$_5$-maleimide (Dojindo Laboratories) or Biotin-ACs Sulfo-OSu (Dojindo Laboratory). The buffers of the cytokines after the biotinylation treatment were replaced with PBS (Sigma-Aldrich Corp.) by dialysis.

Example 2

Isolation of Anti-Human IL-18 Antibody

An scFv phage display library prepared by using human VH and VL cDNAs from mRNAs derived from human B cells (e.g., tonsil or spleen) was screened to isolate antibodies against human IL-18. The antibody library used was an excellent one comprising $10^{11}$ or more diverse antibody molecules.

The biotinylated human IL-18 was bound to BIOMAG Binding Streptavidin (Polysciences, Inc.) by using standard procedures to obtain scFv phages specifically binding to human IL-18 (Non Patent Literature 28). The clones of the obtained scFv phages were designated as "4A6D" and "4A6S". The binding activity of the obtained scFv phages was evaluated by the following method:

Example 3

Binding Activity Test on Anti-IL-18 Antibody

The binding activity of the obtained scFv phages, scFv, and IgG prepared by a standard method (conventional method) was evaluated by ELISA. The biotinylated human IL-18 or the biotinylated mouse IL-18 was diluted to 1 μg/mL with PBS (Sigma-Aldrich Corp.), added at 100 μL/well to Streptavidin plates (Nunc), and incubated at room temperature for 2 hours to immobilize the IL-18. After the immobilization, the plates were washed with PBST, and each obtained scFv phage, scFv, or IgG was added at 100 μL/well to the plates and incubated at 37° C. After 1 hour, the plates were washed with PBST, and a detection antibody anti-M13/HRP (GE Healthcare Japan Corp.), anti-His tag/HRP (Bethyl Laboratories, Inc.), anti-V5 tag/HRP (Bethyl Laboratories, Inc.), anti-mouse IgG/HRP (Invitrogen Corp.), or anti-hFc/HRP (Cosmo Bio Co., Ltd., The binding site) was added at 100 μL/well to the plates and incubated at 37° C. After 1 hour, the plates were washed with PBST, and TMB (Sigma-Aldrich Corp.) was added at 100 μL/well to the plates to develop color. After 30 minutes, the reaction was terminated with 2 N sulfuric acid, and the color values (O.D. 450 nm/650 nm) were measured using a microplate reader (Molecular Devices, Inc.).

The binding activity of the IgG molecule-type 4A6D against human IL-18 and the binding activity of the IgG molecule-type 4A6S against human IL-18 are shown in FIG. 1. 4A6D and 4A6S significantly had binding activity against human IL-18, as compared with a negative control antibody (human anti-HBs antibody).

Example 4

Sequence Analysis of Anti-IL-18 Antibody

The nucleotide sequences of the obtained anti-IL-18 antibodies were confirmed. The DNA nucleotide sequences of VH chain and VL chain genes of the isolated scFv genes were determined by using BIGDYE Terminator v3.1 Cycle Sequencing Kit (Applied Biosystems).

The nucleotide sequences and amino acid sequences of 4A6D and 4A6S are shown in SEQ ID NOs: 1 and 2.

The amino acid sequences of the VH chain and VL chain of 4A6D are shown in SEQ ID NOs: 3 and 4 of Table 1, and the amino acid sequences of the VH chain and VL chain of 4A6S are shown in SEQ ID NOs: 5 and 6. Sites differing between the amino acid sequences of 4A6D and 4A6S are underlined.

TABLE 1

| Clone name | Region | Amino acid sequence | SEQ ID NO |
|---|---|---|---|
| 4A6D | VH | EVQLVESGGGLVQPGGSMRLSCTASGFTF<u>D</u>EYAMSWVRQ APGKGLEWVSGISTGGGGTYYADSVEGRFTISRDNSKNTL YLQMNSLRAEDTAVYYCAKPWLSGSRSGDFWGQGTLVT VSS | SEQ ID NO 3 |
| | VL | QSALTQPASVSGSPGQSITISCTGTSSDVGGYNYVSWYQQ HPGKAPKLLIYEVSHRPSGVSDRFSGSKSGNTASLTISGLQ AEDEADYYCSSFTSSSSLYVFGTGTKLTVL | SEQ ID NO 4 |
| 4A6S | VH | EVQLVESGGGLVQPGGSMRLSCTASGFTF<u>S</u>EYAMSWVRQ APGKGLEWVSGISTGGGGTYYADSVEGRFTISRDNSKNTL YLQMNSLRAEDTAVYYCAKPWLSGSRSGDFWGQGTLVT VSS | SEQ ID NO 5 |
| | VL | QSALTQPASVSGSPGQSITISCTGTSSDVGGYNYVSWYQQ HPGKAPKLLIYEVSHRPSGVSDRFSGSKSGNTASLTISGLQ AEDEADYYCSSFTSSSSLYVFGTGTKLTVL | SEQ ID NO 6 |

The amino acid sequences of CDRs (complementarity determining regions) important for the binding activity of 4A6D and 4A6S are shown in SEQ ID NOs: 7 to 12 of Table 2.

TABLE 2

| Region | | Amino acid sequence | SEQ ID NO |
|---|---|---|---|
| VH | CDR1 | EYAMS | SEQ ID NO 7 |
| | CDR2 | GISTGGGGTYYADSVEG | SEQ ID NO 8 |
| | CDR3 | PWLSGSRSGDF | SEQ ID NO 9 |
| VL | CDR1 | TGTSSDVGGYNYVS | SEQ ID NO 10 |
| | CDR2 | EVSHRPS | SEQ ID NO 11 |
| | CDR3 | SSFTSSSSLYV | SEQ ID NO 12 |

Example 5

IL-18 Receptor Binding Assay (5-1) IL-18 Receptor Binding Assay by ELISA

In order to evaluate the functions of the anti-human IL-18 antibody, an IL-18 receptor binding assay system was constructed.

IL-18Rβ-hFc (R&D Systems, Inc.) was added at 100 μL/well at a concentration of 1 μg/mL to COVALINK plates (Nunc) and incubated at room temperature for 1 hour and then incubated overnight at 4° C. On the next day, the plates were washed with PBS (phosphate buffered saline) and blocked with 1% BSA (bovine serum albumin)-PBS. Human IL-18 (MBL Medical & Biological Laboratories, Co., Ltd.) was prepared at a concentration of 0.5 μg/mL with 1% BSA-PBS, and IL-18Rα-hFc-His (R&D Systems, Inc.) was prepared at a concentration of 2 μg/mL with 1% BSA-PBS. Both of the solutions were mixed (50 μL each). The obtained anti-IL-18 antibody was further added to the IL-18/IL-18Rα-hFc-His mixed solution. This mixed solution was added to the IL-18Rβ-hFc-immobilized COVALINK plates and incubated at 37° C. for 1 hour. After 1 hour, the plates were washed with PBST (phosphate buffered saline-TWEEN 20), and a detection antibody anti-His tag/HRP (Bethyl Laboratories, Inc.) was added at 100 μL/well to the plates and incubated at 37° C. After 1 hour, the plates were washed with PBST, and TMB (Sigma-Aldrich Corp.) was added at 100 μL/well to the plates to develop color. After 30 minutes, the reaction was terminated with 2 N sulfuric acid, and the color values (O.D. 450 nm/650 nm) were measured using a microplate reader (Molecular Devices, Inc.).

Figure 2:
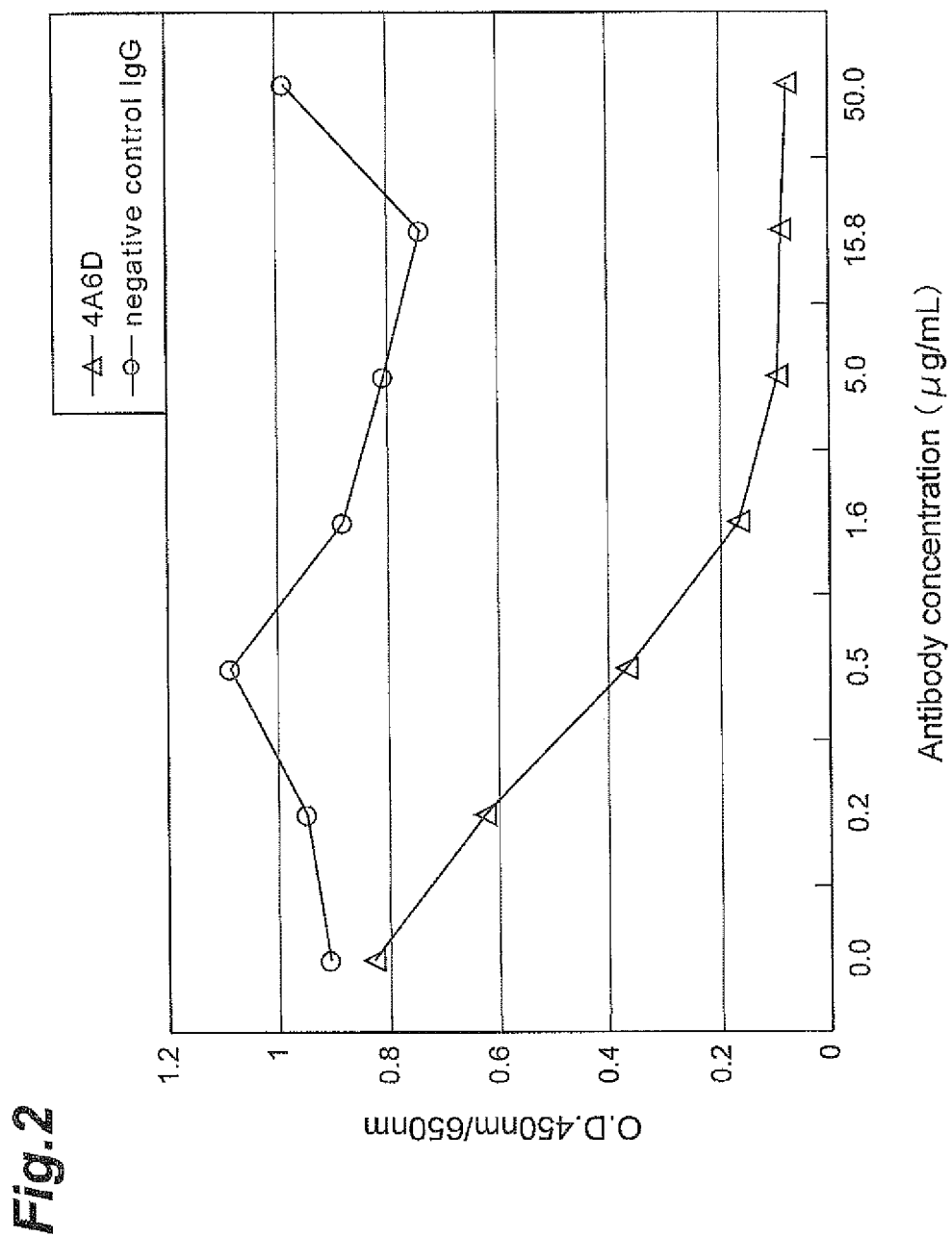
FIG. 2 is a graph showing results of IL-18 receptor binding assay by ELISA.

The inhibitory activity of 4A6D against the binding between human IL-18 and IL-18 receptor is shown in FIG. 2. 4A6D significantly inhibited the binding between human IL-18 and IL-18 receptor, as compared with a negative control antibody (human anti-HBs antibody).

(5-2) IL-18 Receptor Binding Assay Using KG-1 Cell

In order to confirm the ability of the obtained anti-IL-18 antibody to inhibit the binding to native IL-18 receptor, an IL-18 receptor binding assay system was constructed by using KG-1 cells (ATCC #CCL-246).

Human IL-18 (MBL Medical & Biological Laboratories, Co., Ltd.) was diluted to 100 ng/mL with 1% BSA-PBS-0.05% $NaN_3$-2% rabbit serum, mixed with the obtained anti-IL-18 antibody, and incubated at room temperature for 60 minutes. Then, the human IL-18/anti-IL-18 antibody mixed solution was added to KG-1 cells ($1\times10^5$ cells) cultured by a standard technique (e.g., a medium in which an RPMI1640 medium was supplemented with 10% bovine serum, 2 mM L-glutamine, 50 U/mL penicillin, and 50 μg/mL streptomycin), and reacted on ice. After 30 minutes, the supernatant was removed by centrifugation (1200 rpm, 3 min, 4° C.), and a biotinylated anti-IL-18 antibody 125-2H (MBL Medical & Biological Laboratories, Co., Ltd.) not inhibiting the binding between IL-18 and IL-18 receptor was added thereto and reacted on ice. After 30 minutes, the supernatant was removed by centrifugation (1200 rpm, 3 min, 4° C.), and streptavidin-PE (BD Becton, Dickinson and Company) was added thereto and reacted on ice for 30 minutes. After the reaction, the supernatant was removed by centrifugation (1200 rpm, 3 min, 4° C.), and the KG-1 cells were floated with 1% BSA-PBS-0.05% $NaN_3$-2% rabbit serum. The fluorescence intensity in the reacted KG-1 cells was measured using FACSCAN (BD Becton, Dickinson and Company).

Figure 3:
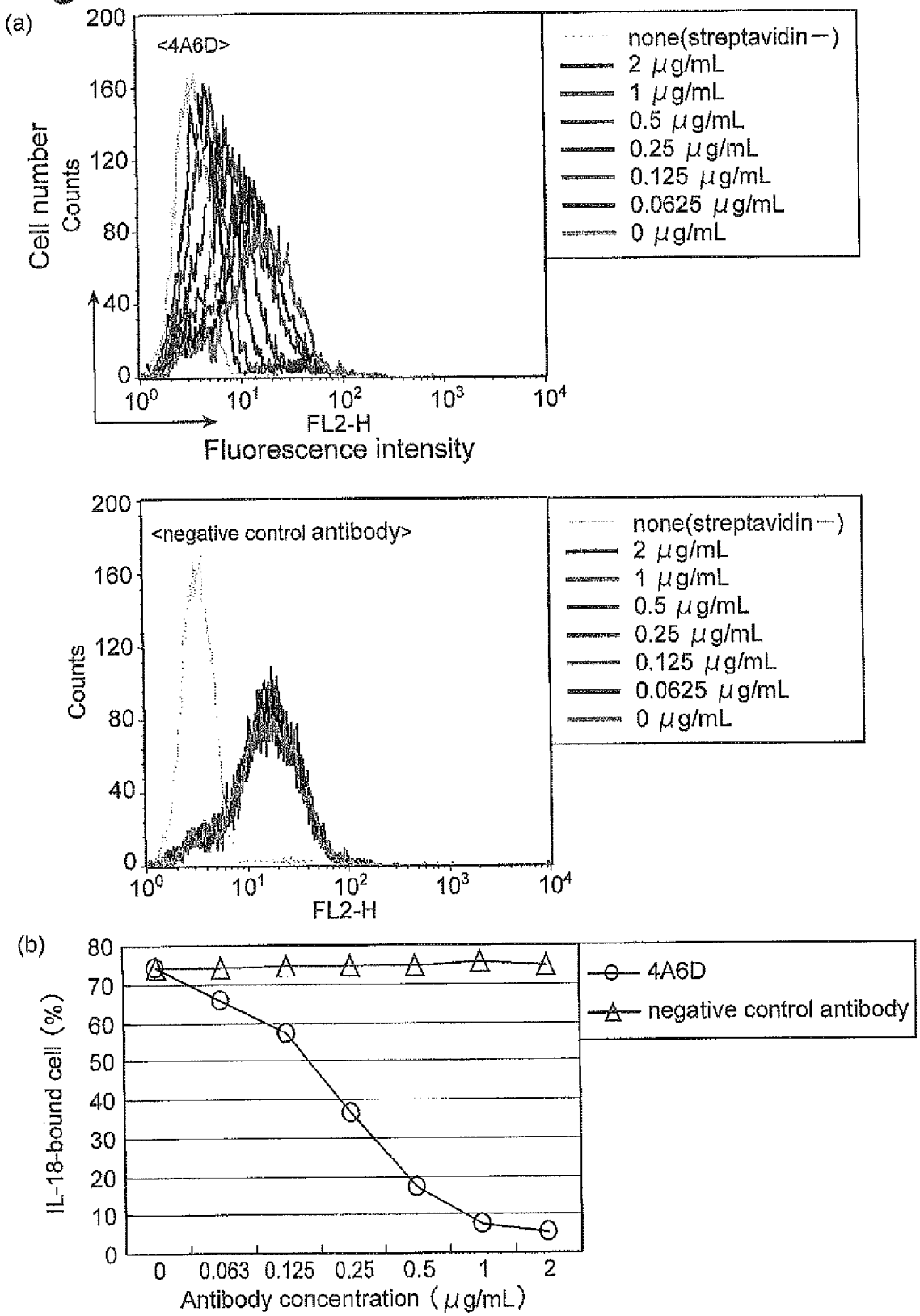
FIG. 3 Each of FIGS. 3 (a) and 3(b) is a graph showing results of IL-18 receptor binding assay using KG-1 cells.

The inhibitory activity of the IgG molecule-type 4A6D against the binding between human IL-18 and native IL-18 receptor is shown in FIGS. 3(a) and 3(b). The IgG molecule-type 4A6D significantly inhibited the binding between human IL-18 and IL-18 receptor, as compared with a negative control antibody (human anti-HBs antibody).

Example 6

Neutralization Test on Anti-IL-18 Antibody (6-1) Neutralization Test Using Recombinant IL-18

In order to test the neutralizing activity of each anti-human IL-18 antibody, a neutralization test confirmed in the art as a test for monitoring IL-18 activity was conducted.

Briefly speaking, the neutralization test employs KG-1 cells (ATCC #CCL-246) cultured by a standard technique (e.g., a medium in which an RPMI1640 medium was supplemented with 10% bovine serum, 2 mM L-glutamine, 50 U/mL penicillin, and 50 μg/mL streptomycin). In order to conduct the neutralization test, the KG-1 cells were inoculated at $3\times10^5$ cells/mL and cultured (37° C., 5% $CO_2$) for 4 days. After 4 days, the KG-1 cells were prepared at $3\times10^6$ cells/mL, and recombinant IL-18 and the obtained anti-IL-18 antibody were added thereto at final concentrations of 4 ng/mL, followed by culture for 24 hours (37° C., 5% $CO_2$). After 24 hours, the culture supernatant was recovered, and the amount of IFN-γ produced was detected with a commercially available IFN-γ quantitative ELISA kit (Invitrogen Corp.) according to the instruction of the manufacturer.

Figure 4:
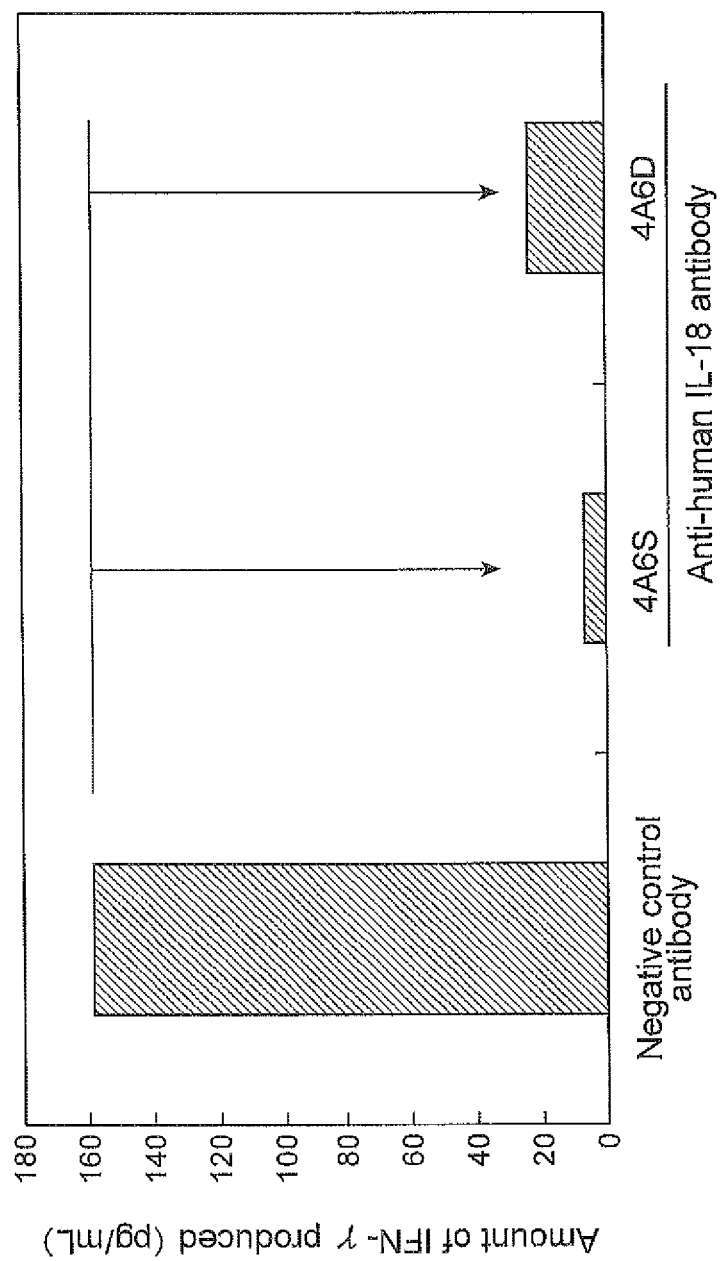
FIG. 4 is a graph showing results of a neutralization test using recombinant IL-18.

As a result, as shown in FIG. 4, the IgG molecule-type 4A6D and 4A6S inhibited IFN-γ production from the KG-1 cells. Results of further calculating $IC_{50}$ of 4A6D and 4A6S are shown in Table 3. The $IC_{50}$ values of 4A6D and 4A6S were 0.007 nM and 0.013 nM, respectively. This demonstrated that 4A6D and 4A6S are far superior in neutralizing ability to previously reported IL-18 inhibitors.

TABLE 3

| Clone name | Neutralizing ability ($IC_{50}$, nM) |
| --- | --- |
| 4A6D | 0.007 |
| 4A6S | 0.013 |
| ABT-325 *1 | 0.2 |
| 2C10 *2 | 0.1 |
| IL-18BP *3 | 0.4 |
| H18.108 *4 | 5 |

*1 described in Patent Literature 2.
*2 described in Patent Literature 3 or 4.
*3 described in Non Patent Literature 29.
*4 described in Patent Literature 5 and Non Patent Literature 30.

(6-2) Neutralization Test Using Human Cell-derived Natural IL-18

KG-1 cells (ATCC #CCL-246) and THP-1 cells (ATCC #TIB-202) cultured by a standard technique (e.g., a medium in which an RPMI1640 medium was supplemented with 10% bovine serum, 2 mM L-glutamine, 50 U/mL penicillin, and 50 μg/mL streptomycin) were used. In order to conduct the neutralization test, the KG-1 cells were inoculated at $3\times10^5$ cells/mL and cultured (37° C., 5% $CO_2$) for 4 days. Also, the THP-1 cells were inoculated at $3\times10^5$ cells/mL and cultured (37° C., 5% $CO_2$) for 2 days. After the culture, the KG-1 cells and the THP-1 cells were prepared at $6\times10^6$ cells/mL and $1\times10^6$ cells/mL, respectively, and mixed in equal amounts. LPS (lipopolysaccharide, Sigma-Aldrich Corp.) and the obtained anti-IL-18 antibody were added thereto at final concentrations of 1 μg/mL, followed by culture for 24 hours (37° C., 5% $CO_2$). After 24 hours, the culture supernatant was recovered, and the amount of IFN-γ produced was detected with a commercially available IFN-γ quantitative ELISA kit (Invitrogen Corp.) according to the instruction of the manufacturer.

The results are shown in Table 4. IFN-γ was not produced even by adding LPS to the THP-1 cells and the KG-1 cells alone, whereas IFN-γ was produced only when all of THP-1, KG-1, and LPS were present. Furthermore, IFN-γ production was inhibited by adding 4A6D and 4A6S. These results demonstrated that natural IL-18 is produced by using two types of human cells, and as a result, the assay system for producing IFN-γ is constructed. Also, these results demonstrated that the IgG molecule-type 4A6D and 4A6S inhibit human cell-derived natural IL-18.

TABLE 4

| THP-1 | KG-1 | LPS | Antibody | Amount of IFN-γ produced (pg/mL) |
|---|---|---|---|---|
| + | − | − | − | 9 |
| − | + | − | − | 9 |
| + | + | − | − | 28 |
| + | + | + | − | 144 |
| + | − | + | − | 22 |
| − | + | + | − | 15 |
| + | + | + | 4A6D | 33 |
| + | + | + | 4A6S | 36 |
| + | + | + | Negative control | 134 |

(6-3) Neutralization Test Using Chymase Cleavage-type IL-18

Chymase cleavage-type IL-18 was prepared according to the previous report (Non Patent Literature 9).

Briefly speaking, a precursor proIL-18 was expressed with *Escherichia coli* as a host and purified. Chymase (Funakoshi Corp.) was added at 10 U to the prepared proIL-18 (100 µg/mL) and incubated at 37° C. for 80 minutes. This was used as chymase cleavage-type IL-18.

On the other hand, KG-1 cells were inoculated at $3\times10^5$ cells/mL and cultured (37° C., 5% $CO_2$) for 4 days. After 4 days, the KG-1 cells were prepared at $3\times10^6$ cell/mL. The chymase cleavage-type IL-18 was added at a 1/20 volume of the reaction system, and the obtained anti-IL-18 antibody was further added thereto, followed by culture for 24 hours (37° C., 5% $CO_2$). After 24 hours, the culture supernatant was recovered, and the amount of IFN-γ produced was detected with a commercially available IFN-γ quantitative ELISA kit (Invitrogen Corp.) according to the instruction of the manufacturer.

The results are shown in Table 5. IFN-γ production was inhibited by adding the IgG molecule-type 4A6D and 4A6S. This result demonstrated that 4A6D and 4A6S inhibit chymase-cleavage type active-form IL-18.

TABLE 5

| proIL-18 | chymase | Antibody | Amount of IFN-γ produced (pg/mL) |
|---|---|---|---|
| + | + | − | 91 |
| + | − | − | 18 |
| − | + | − | 22 |
| + | + | 4A6D | 22 |
| + | + | 4A6S | 26 |
| + | + | Negative control | 109 |

Example 7

Epitope Analysis (Competitive ELISA)

Epitope analysis on the obtained anti-IL-18 antibody was conducted by competitive ELISA.

The biotinylated human IL-18 was diluted to 1 µg/mL with PBS (Sigma-Aldrich Corp.), added at 100 µL/well to Streptavidin plates (Nunc), and incubated at room temperature for 2 hours to immobilize the human IL-18. After the immobilization, the plates were washed with PBST, and anti-mouse α9 scFv-mFc (negative control) or 4A6D scFv-mFc was added at 100 µL/well to the plates and incubated at 37° C. After 1 hour, human IL-18BPa-hFc (R&D Systems, Inc.) was prepared at 30 ng/mL with 1% BSA-PBS, added at 100 µL/well to the plates, and incubated at 37° C. After 1 hour, the plates were washed with PBST, and a detection antibody anti-hFc/HRP (Cosmo Bio Co., Ltd., The binding site) was added at 100 µL/well to the plates and incubated at 37° C. After 1 hour, the plates were washed with PBST, and TMB (Sigma-Aldrich Corp.) was added at 100 µL/well to the plates to develop color. After 30 minutes, the reaction was terminated with 2 N sulfuric acid, and the color values (O.D. 450 nm/650 nm) were measured using a microplate reader (Molecular Devices, Inc.).

Figure 5:
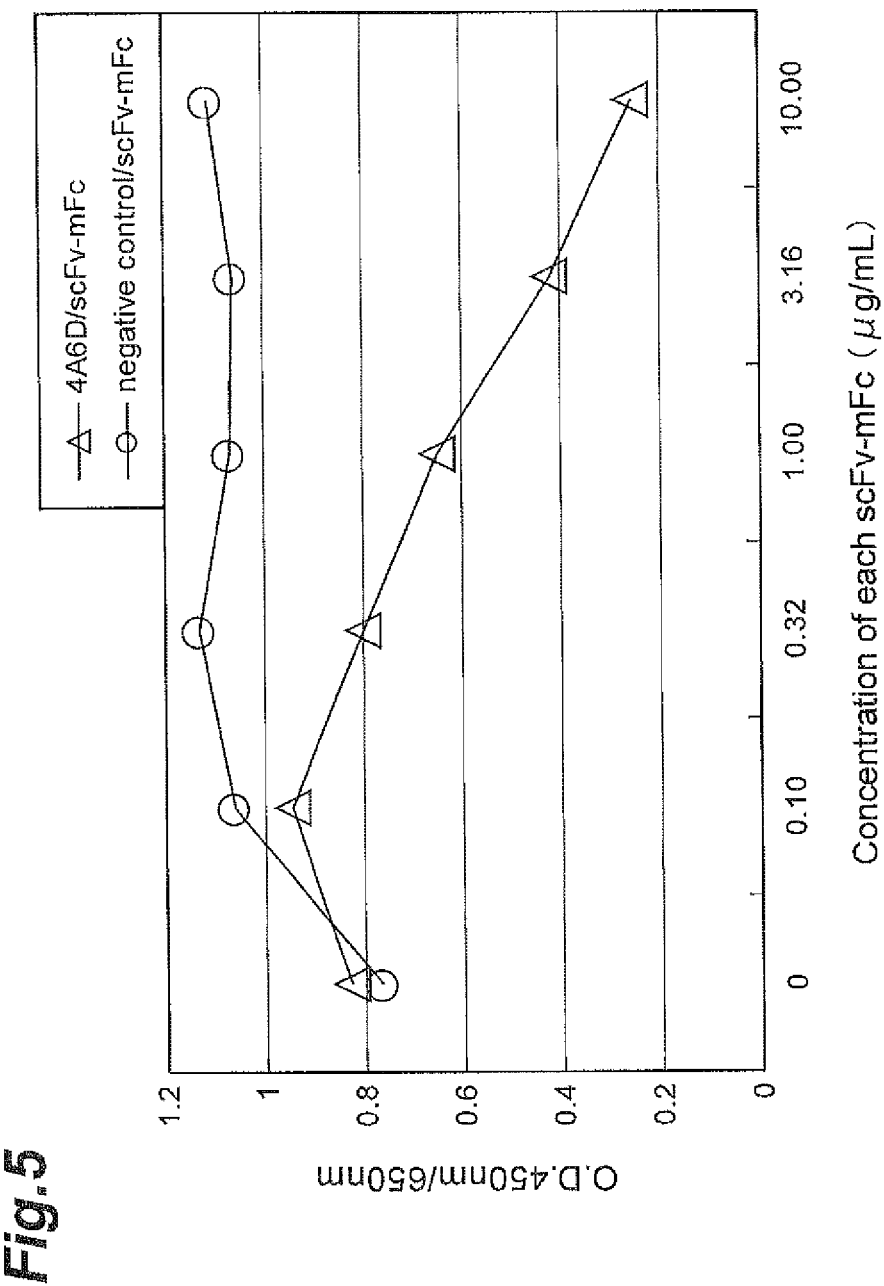
FIG. 5 is a graph showing results of epitope analysis on an anti-human IL-18 antibody by competitive ELISA.

The results of the epitope analysis on the anti-human IL-18 antibody are shown in FIG. 5. 4A6D was found to compete with human IL-18BPa-hFc. This means that 4A6D and human IL-18BPa recognize the same epitope and 4A6D has an inhibition manner similar to that in vivo.

Example 8

IL-18 Receptor Binding Assay in Presence of Anti-Human IL-18 Antibody and IL-18BP On the basis of above "IL-18 receptor binding assay using KG-1 cell", human IL-18BPa-Fc (R&D Systems, Inc.) was added at the same time with the obtained anti-IL-18 antibody to test whether their effects were synergistic.

Figure 6:
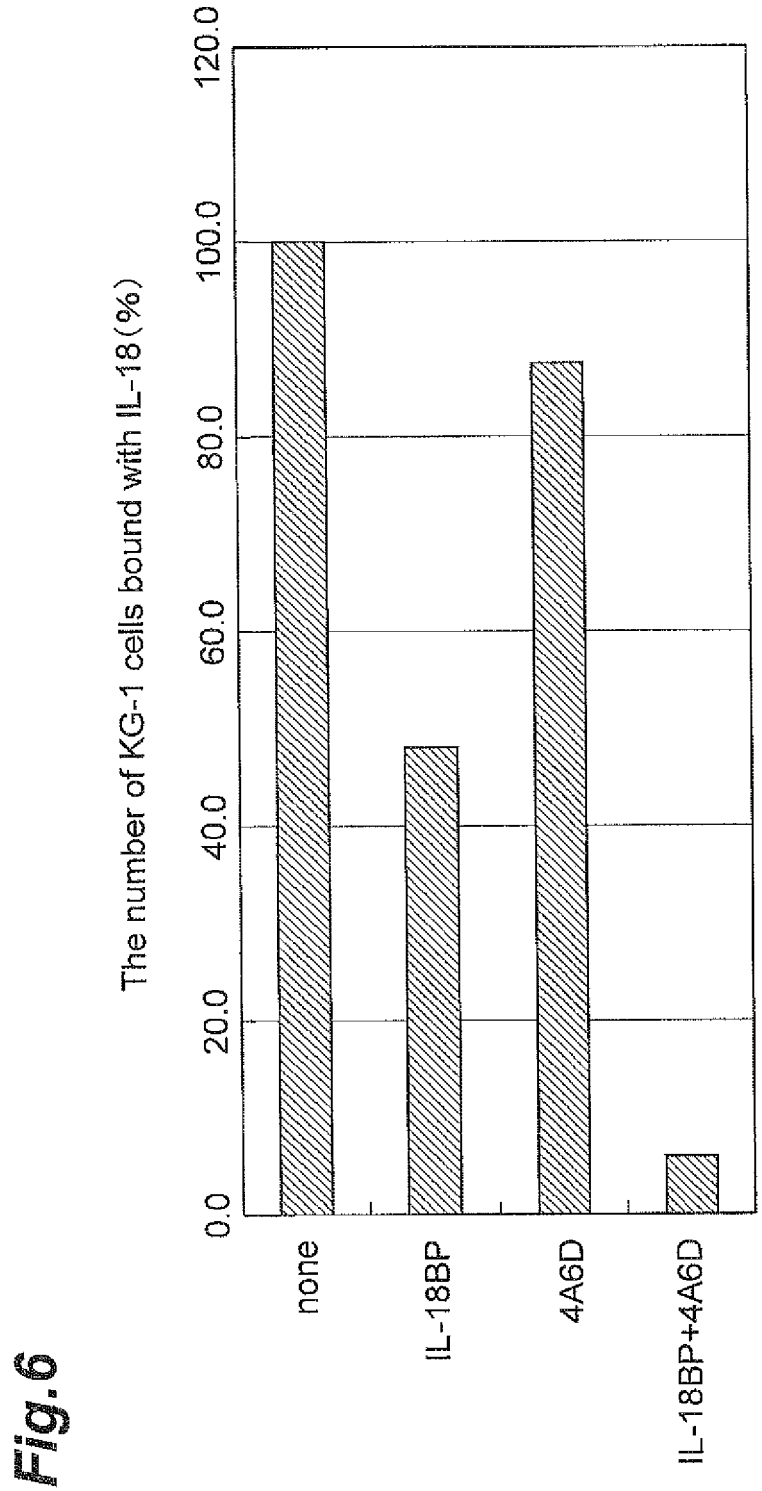
FIG. 6 is a graph showing results of IL-18 receptor binding assay in the presence of an anti-human IL-18 antibody and IL-18BP.

The results are shown in FIG. 6. The IgG molecule-type 4A6D and human IL-18BPa each alone inhibited the binding of IL-18 to the KG-1 cells by tens of %, whereas the coexistence thereof exhibited a higher inhibitory effect than that by the addition of each alone.

Example 9

Cross-Reactivity Test

The biotinylated human IL-18 (MBL Medical & Biological Laboratories, Co., Ltd.), the biotinylated monkey IL-18 (Thermo Fisher Scientific K.K.), the biotinylated rat IL-18 (Acris Antibodies GmbH), the biotinylated mouse IL-18 (MBL Medical & Biological Laboratories, Co., Ltd.), the biotinylated human IL-1β(Funakoshi Corp.), and the biotinylated human IL-33 (MBL Medical & Biological Laboratories, Co., Ltd.) described in above "Biotinylation of cytokine" were each diluted to 1 µg/mL with PBS (Sigma-Aldrich Corp.), added at 100 µL/well to Streptavidin plates (Nunc), and incubated at room temperature for 2 hours to immobilize these various cytokines. After the immobilization, the plates were washed with PBST, and each obtained antibody was added at 100 µL/well to the plates and incubated at 37° C. After 1 hour, the plates were washed with PBST, and a detection antibody anti-mouse IgG/HRP (Invitrogen Corp.) or anti-hFc/HRP (Cosmo Bio Co., Ltd., The binding site) was added at 100 μL/well to the plates and incubated at 37° C. After 1 hour, the plates were washed with PBST, and TMB (Sigma-Aldrich Corp.) was added at 100 μL/well to the plates to develop color. After 30 minutes, the reaction was terminated with 2 N sulfuric acid, and the color values (O.D. 450 nm/650 nm) were measured using a microplate reader (Molecular Devices, Inc.).

The results are shown in Table 6. The obtained anti-human IL-18 antibodies 4A6D and 4A6S exhibited binding activity against human and monkey IL-18, but did not exhibit binding activity against rat and mouse IL-18. On the other hand, the obtained anti-IL-18 antibodies lacked binding activity against IL-1β and IL-33, which were other members of the IL-1 family.

TABLE 6

| Anti-IL-18 antibody clone name | Various cytokines | | | | | |
|---|---|---|---|---|---|---|
| | Human IL-18 | Monkey IL-18 | Rat IL-18 | Mouse IL-18 | Human IL-1β | Human IL-33 |
| 4A6D | + | + | − | − | − | − |
| 4A6S | + | + | − | − | − | − |

Example 10

Epitope Analysis (Reactivity Analysis Using Ala Substitution Variant)

Wild-type human IL-18 or a K53A variant of human IL-18 were expressed as a GST fusion protein containing a factor Xa cleavage site as a linker, with *Escherichia coli* as a host, and bound to a glutathione SEPHAROSE 4B (GE Healthcare Japan Corp.) column. Then, the wild-type human IL-18 or the K53A variant of human IL-18 was eluted by adding factor Xa. The factor Xa contained in the eluate was removed by using XARREST agarose (Novagen). This eluate was used as the wild-type human IL-18 or the K53A variant of human IL-18.

Next, these human IL-18 proteins were biotinylated, then each diluted to 1 μg/mL with PBS (Sigma-Aldrich Corp.), added at 100 μL/well to Streptavidin plates (Nunc), and incubated at room temperature for 2 hours to immobilize them. After the immobilization, the plates were washed with PBST, and human IL-18BPa-hFc (R&D Systems, Inc.) or the IgG molecule-type 4A6D was prepared at 1 μg/mL with 1% BSA-PBS, added at 100 μL/well to the plates, and incubated at 37° C. After 1 hour, the plates were washed with PBST, and a detection antibody anti-hFc/HRP (Cosmo Bio Co., Ltd., The binding site) was added at 100 μL/well to the plates and incubated at 37° C. After 1 hour, the plates were washed with PBST, and TMB (Sigma-Aldrich Corp.) was added at 100 μL/well to the plates to develop color. After 30 minutes, the reaction was terminated with 1 M sulfuric acid, and the color values (O.D. 450 nm/650 nm) were measured using a microplate reader (Molecular Devices, Inc.).

Figure 7:
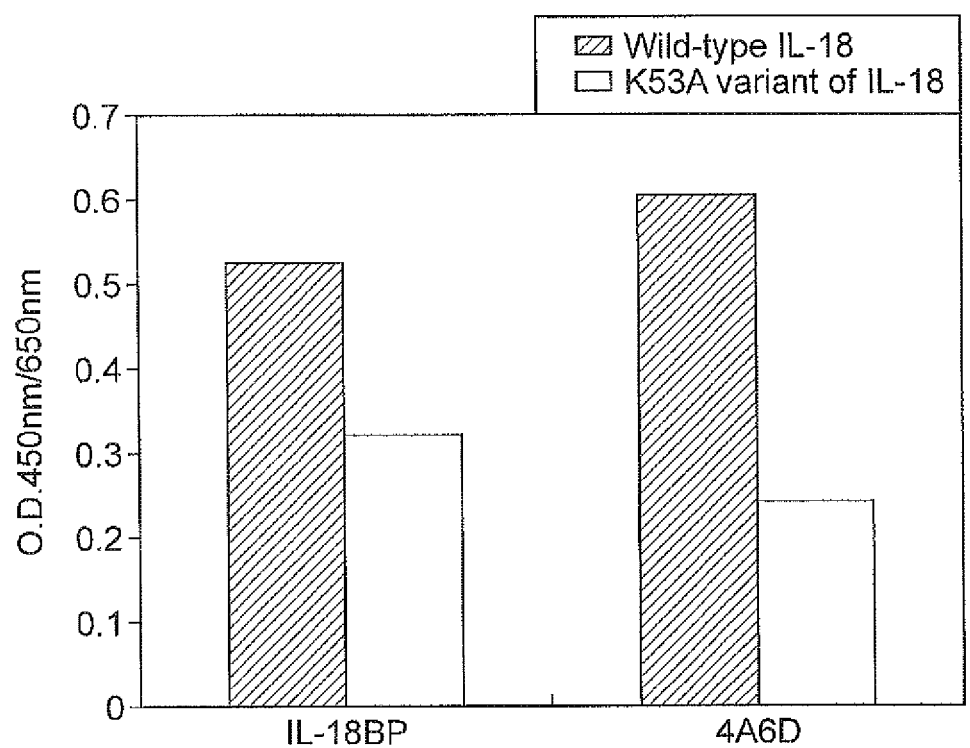
FIG. 7 is a graph showing results of epitope analysis on an anti-IL-18 antibody using a K53A variant of IL-18.

The results of ELISA are shown in FIG. 7. As with human IL-18BPa-hFc, 4A6D has reduced reactivity with the K53A variant of human IL-18 compared with the wild-type human IL-18. This means that lysine, which is an amino acid residue at the position 53 of human IL-18, is important as an epitope for 4A6D, and indicates that human IL-18BPa also recognizes this region. Specifically, it was shown that 4A6D recognizes, as an epitope, the same region as the recognition site of human IL-18BPa.

Example 11

Analysis on Reactivity with Complex of IL-18 and IL-18BP

The reactivity of the anti-IL-18 antibody obtained by ELISA with a complex of IL-18 and IL-18BP was evaluated.

The biotinylated human IL-18 was diluted to 1 μg/mL with PBS (Sigma-Aldrich Corp.), added at 100 μL/well to Streptavidin plates (Nunc), and incubated at room temperature for 1 hour to immobilize the human IL-18. The plates were washed with PB ST, and human IL-18BPa-hFc (R&D Systems, Inc.) diluted to 10 μg/mL with 1% BSA-PBS was added at 100 μL/well to the plates and incubated at 37° C. for 1 hour to form a complex of IL-18 and IL-18BP. The plates were washed with PBST, and 4A6D scFv-mFc was added at 100 μL/well to the plates and incubated at 37° C. After 1 hour, the plates were washed with PBST, and a detection antibody anti-mouse IgG/HRP (Invitrogen Corp.) was added at 100 μL/well to the plates and incubated at 37° C. After 1 hour, the plates were washed with PBST, and TMB (Sigma-Aldrich Corp.) was added at 100 μL/well to the plates to develop color. After 30 minutes, the reaction was terminated with 1 M sulfuric acid, and the color values (O.D. 450 nm/650 nm) were measured using a microplate reader (Molecular Devices, Inc.).

Figure 8:
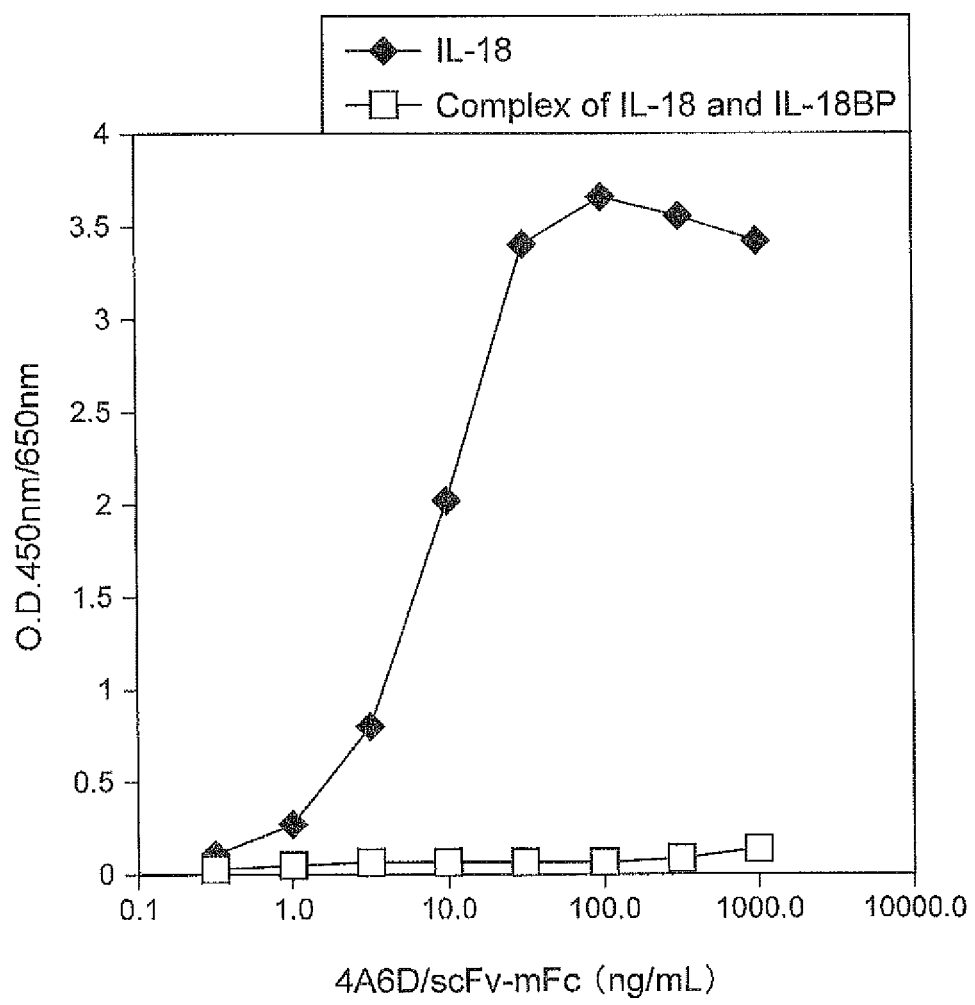
FIG. 8 is a graph showing results of analysis on the reactivity of an anti-human IL-18 antibody with a complex of IL-18 and IL-18BP.

The results of the analysis on the reactivity with the complex of IL-18 and IL-18BP are shown in FIG. 8. 4A6D bound to IL-18, but did not react with the complex of IL-18 and IL-18BP.

INDUSTRIAL APPLICABILITY

The antibody of the present invention against human IL-18 and the fragment thereof are applicable to a disease in which human IL-18 is involved directly or indirectly.

The invention claimed is:

1. An anti-human interleukin-18 (IL-18) antibody or a human IL-18-binding fragment thereof, wherein said antibody or IL-18-binding fragment thereof comprises a heavy chain variable region and a light chain variable region, wherein:
   the heavy chain variable region comprises heavy chain variable region complementarity determining regions CDR1, CDR2, and CDR3 comprising the amino acid sequences set forth in SEQ ID NO:7, SEQ ID NO:8, and SEQ ID NO:9, respectively; and
   the light chain variable region comprises light chain variable region complementarity determining regions CDR1, CDR2, and CDR3 comprising the amino acid sequences set forth in SEQ ID NO:10, SEQ ID NO:11, and SEQ ID NO:12, respectively.

2. The anti-human IL-18 antibody or the human IL-18-binding fragment thereof according to claim 1, wherein the heavy chain variable region is at least 90% identical to SEQ ID NO:3 and the light chain variable region is at least 90% identical to SEQ ID NO:4.

3. The anti-human IL-18 antibody or the human IL-18-binding fragment thereof according to claim 1, wherein the heavy chain variable region is at least 90% identical to SEQ ID NO:5 and the light chain variable region is at least 90% identical to SEQ ID NO:6.

4. The anti-human IL-18 antibody or the human IL-18-binding fragment thereof according to claim 1, wherein the heavy chain variable region comprises the amino acid sequence of SEQ ID NO:3 and the light chain variable region comprises the amino acid sequence of SEQ ID NO:4.

5. The anti-human IL-18 antibody or the human IL-18-binding fragment thereof according to claim 1, wherein the heavy chain variable region comprises the amino acid sequence of SEQ ID NO:5 and the light chain variable region comprises the amino acid sequence of SEQ ID NO:6.

6. The anti-human IL-18 antibody or the human IL-18-binding fragment thereof according to claim 1, wherein the antibody or the human IL-18-binding fragment thereof comprises a heavy chain comprising a constant region of a human-derived antibody and a light chain comprising a constant region of a human-derived antibody.

7. The anti-human IL-18 antibody or the human IL-18-binding fragment thereof according to claim 4, wherein the antibody or the human IL-18-binding fragment thereof comprises a heavy chain comprising a constant region of a human-derived antibody and a light chain comprising a constant region of a human-derived antibody.

8. The anti-human IL-18 antibody or the human IL-18-binding fragment thereof according to claim 5, wherein the antibody or the human IL-18-binding fragment thereof comprises a heavy chain comprising a constant region of a human-derived antibody and a light chain comprising a constant region of a human-derived antibody.

9. The human IL-18-binding fragment according to claim 1.

10. The human IL-18-binding fragment according to claim 4.

11. The human IL-18-binding fragment according to claim 5.

12. The human IL-18-binding fragment according to claim 9, wherein the fragment is a single-chain variable fragment (scFv), Fab, Fab', F(ab)'$_2$, scAb, or scFvFc.

13. The human IL-18-binding fragment according to claim 10, wherein the fragment is a scFv, Fab, Fab', F(ab)'2, scAb, or scFvFc.

14. The human IL-18-binding fragment according to claim 11, wherein the fragment is a scFv, Fab, Fab', F(ab)'2, scAb, or scFvFc.

15. A pharmaceutical composition comprising the anti-human IL-18 antibody or the human IL-18-binding fragment thereof according to claim 1 and a pharmaceutically acceptable carrier.

16. A pharmaceutical composition comprising the anti-human IL-18 antibody or the human IL-18-binding fragment thereof according to claim 4 and a pharmaceutically acceptable carrier.

17. A pharmaceutical composition comprising the anti-human IL-18 antibody or the human IL-18-binding fragment thereof according to claim 5 and a pharmaceutically acceptable carrier.

* * * * *